United States Patent
Bendall

(10) Patent No.: US 9,818,039 B2
(45) Date of Patent: Nov. 14, 2017

(54) METHOD AND DEVICE FOR AUTOMATICALLY IDENTIFYING A POINT OF INTEREST IN A DEPTH MEASUREMENT ON A VIEWED OBJECT

(71) Applicant: General Electric Company, Schenectady, NY (US)

(72) Inventor: Clark Alexander Bendall, Syracuse, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 15/018,556

(22) Filed: Feb. 8, 2016

(65) Prior Publication Data

US 2016/0171705 A1 Jun. 16, 2016

Related U.S. Application Data

(63) Continuation-in-part of application No. 14/108,976, filed on Dec. 17, 2013.

(51) Int. Cl.
*G06K 9/32* (2006.01)
*G06T 7/00* (2017.01)
(Continued)

(52) U.S. Cl.
CPC ............ *G06K 9/3233* (2013.01); *G01B 11/03* (2013.01); *G01B 11/22* (2013.01); *G01B 11/24* (2013.01);
(Continued)

(58) Field of Classification Search
CPC ....... G06T 17/00; G06T 7/001; G06T 7/0012; G06T 7/0051; G06T 7/0063;
(Continued)

(56) References Cited

U.S. PATENT DOCUMENTS 3,657,638 A * 4/1972 Holler .................... G01N 27/83
324/213
4,188,122 A * 2/1980 Massie ..................... G01J 9/04
356/489
(Continued)

FOREIGN PATENT DOCUMENTS

CN 1158684 A 9/1997
EP 30549182 A2 6/1993
(Continued)

OTHER PUBLICATIONS

Yerex et al. "Predictive Display Models for Tele-Manipulation from Uncalibrated Camera-Capture of Scene Geometry and Appearance", IEEE 2003.
(Continued)

*Primary Examiner* — Manav Seth
(74) *Attorney, Agent, or Firm* — Barclay Damon LLP

(57) ABSTRACT

A method and device for automatically identifying a point of interest in a depth measurement on a viewed object using a video inspection device is disclosed. The video inspect device determines the three-dimensional coordinates in a region of interest on the viewed object and analyzes those surface points to determine the desired measurement application (e.g., determining the deepest point, the highest point, or the clearance between two surfaces). Based on the desired measurement application, the video inspection device automatically identifies the point of interest on the viewed object and places a cursor at that location.

19 Claims, 11 Drawing Sheets

(51) Int. Cl.
*G01B 11/22* (2006.01)
*G01N 21/88* (2006.01)
*G01B 11/03* (2006.01)
*G01B 11/24* (2006.01)
*G06T 19/00* (2011.01)
*H04N 13/00* (2006.01)

(52) U.S. Cl.
CPC ......... *G01N 21/8851* (2013.01); *G06T 7/001* (2013.01); *G06T 19/00* (2013.01); *G01N 2021/8861* (2013.01); *G01N 2021/8887* (2013.01); *G06T 2200/08* (2013.01); *G06T 2207/10028* (2013.01); *H04N 2013/0081* (2013.01)

(58) Field of Classification Search
CPC ......... G06T 7/0067; G06T 2207/10028; G06T 2207/20112; G06T 2207/20096; G06T 19/00; G06T 2200/08; G06T 11/03; G01N 21/8851; G01N 2201/08; G01N 2201/102; G01N 21/8861; G01N 21/8887; G06K 9/00214; G06K 2209/19; G06K 9/3233; G01B 11/24; G01B 11/30; G01B 13/22; G01B 11/03; G01B 11/22
See application file for complete search history.

(56) References Cited

U.S. PATENT DOCUMENTS

| | | | | |
|---|---|---|---|---|
| 4,357,660 A * | 11/1982 | Hepp | ................. | G01V 3/20 324/323 |
| 4,493,105 A | 1/1985 | Beall et al. | | |
| 4,688,184 A * | 8/1987 | Taniguti | ................. | G01B 11/24 356/614 |
| 4,980,763 A | 12/1990 | Lia | | |
| 4,983,836 A * | 1/1991 | Matoba | ................. | G01N 25/72 250/330 |
| 4,988,886 A | 1/1991 | Palum et al. | | |
| 5,066,119 A | 11/1991 | Bertrand | | |
| 5,175,601 A | 12/1992 | Fitts | | |
| 5,198,877 A * | 3/1993 | Schulz | ................. | G01B 11/24 356/141.4 |
| 5,273,429 A * | 12/1993 | Rekow | ................. | A61C 13/0004 433/215 |
| 5,302,999 A | 4/1994 | Oshida et al. | | |
| 5,307,152 A | 4/1994 | Boehnlein et al. | | |
| 5,434,669 A | 7/1995 | Tabata et al. | | |
| 5,510,833 A | 4/1996 | Webb et al. | | |
| 5,581,352 A | 12/1996 | Zeien | | |
| 5,607,607 A * | 3/1997 | Naiman | ................. | A61F 2/02 219/121.61 |
| 5,633,675 A | 5/1997 | Danna et al. | | |
| 5,810,719 A | 9/1998 | Toida | | |
| 5,822,066 A | 10/1998 | Jeong et al. | | |
| 5,823,942 A | 10/1998 | Toida | | |
| 6,011,624 A | 1/2000 | de Groot | | |
| 6,064,759 A | 5/2000 | Buckley et al. | | |
| 6,083,162 A | 7/2000 | Vining | | |
| 6,201,541 B1 | 3/2001 | Shalom et al. | | |
| 6,299,309 B1 * | 10/2001 | Ruiz | ................. | A61F 9/008 351/212 |
| 6,323,952 B1 | 11/2001 | Yomoto et al. | | |
| 6,438,272 B1 | 8/2002 | Huang et al. | | |
| 6,459,481 B1 | 10/2002 | Schaack | | |
| 6,670,962 B2 | 12/2003 | Perry et al. | | |
| 6,674,891 B1 * | 1/2004 | Sameshima | ................. | G01B 11/24 382/152 |
| 6,717,578 B1 | 4/2004 | Deering | | |
| 6,909,988 B2 * | 6/2005 | Batzinger | ................. | B21O 51/00 451/5 |
| 6,945,931 B2 | 9/2005 | Ogawa | | |
| 6,956,576 B1 | 10/2005 | Deering et al. | | |
| 7,030,996 B2 | 4/2006 | De Groot et al. | | |
| 7,286,246 B2 | 10/2007 | Yoshida | | |
| 7,298,499 B2 * | 11/2007 | Fournier | ................. | G01B 11/25 356/237.1 |
| 7,372,558 B2 * | 5/2008 | Kaufman | ................. | G03B 31/00 356/237.2 |
| 7,388,679 B2 | 6/2008 | Yoshino et al. | | |
| 7,453,456 B2 | 11/2008 | Petrov et al. | | |
| 7,474,803 B2 * | 1/2009 | Petrov | ................. | G06K 9/20 345/419 |
| 7,486,805 B2 | 2/2009 | Krattiger | | |
| 7,518,632 B2 | 4/2009 | Konomura | | |
| 7,551,293 B2 | 6/2009 | Yelin et al. | | |
| 7,564,626 B2 | 7/2009 | Bendall et al. | | |
| 7,570,363 B2 | 8/2009 | Petrov et al. | | |
| 7,570,370 B2 | 8/2009 | Steinbichler et al. | | |
| 7,755,817 B2 | 7/2010 | Ho et al. | | |
| 7,782,453 B2 | 8/2010 | Bendall et al. | | |
| 7,812,968 B2 | 10/2010 | Bendall et al. | | |
| 7,821,649 B2 | 10/2010 | Bendall et al. | | |
| 7,855,732 B2 | 12/2010 | Williams et al. | | |
| 7,899,598 B2 | 3/2011 | Woon et al. | | |
| 8,107,083 B2 | 1/2012 | Bendall et al. | | |
| 8,165,351 B2 | 4/2012 | Bendall | | |
| 8,265,425 B2 * | 9/2012 | Ng-Thow-Hing | ................. | G06T 7/0042 382/199 |
| 8,300,920 B2 | 10/2012 | Chang et al. | | |
| 8,411,083 B2 | 4/2013 | Bendall | | |
| 8,422,030 B2 | 4/2013 | Bendall et al. | | |
| 8,443,704 B2 * | 5/2013 | Burke | ................. | B23C 3/30 82/1.11 |
| 8,512,918 B2 * | 8/2013 | Shoki | ................. | B82Y 10/00 430/22 |
| 8,582,207 B2 * | 11/2013 | Fukuda | ................. | C08J 7/047 349/112 |
| 8,686,943 B1 * | 4/2014 | Rafii | ................. | G06F 3/017 345/158 |
| 8,760,447 B2 * | 6/2014 | Bendall | ................. | G06T 7/0004 345/419 |
| 8,810,636 B2 | 8/2014 | Bendall | | |
| 8,849,620 B2 * | 9/2014 | Regan | ................. | G06F 17/50 345/419 |
| 9,013,469 B2 * | 4/2015 | Bendall | ................. | G01B 11/24 345/419 |
| 9,074,868 B2 | 7/2015 | Bendall et al. | | |
| 2001/0018644 A1 | 8/2001 | Schwalb et al. | | |
| 2002/0163573 A1 | 11/2002 | Bieman et al. | | |
| 2004/0189799 A1 | 9/2004 | Spencer | | |
| 2006/0150124 A1 | 7/2006 | Hornegger et al. | | |
| 2006/0232583 A1 | 10/2006 | Petrov et al. | | |
| 2006/0282009 A1 | 12/2006 | Oberg et al. | | |
| 2007/0206204 A1 | 9/2007 | Jia et al. | | |
| 2008/0198159 A1 | 8/2008 | Liu et al. | | |
| 2009/0059242 A1 | 3/2009 | Fujieda et al. | | |
| 2009/0158315 A1 | 6/2009 | Bendall et al. | | |
| 2009/0225320 A1 | 9/2009 | Bendall et al. | | |
| 2009/0225321 A1 | 9/2009 | Bendall et al. | | |
| 2009/0225329 A1 | 9/2009 | Bendall et al. | | |
| 2009/0225333 A1 | 9/2009 | Bendall et al. | | |
| 2010/0284607 A1 | 11/2010 | Van Den Hengel et al. | | |
| 2011/0115730 A1 * | 5/2011 | Kim | ................. | G06F 3/04883 345/173 |
| 2011/0115791 A1 * | 5/2011 | Sabiston | ................. | A61F 2/5046 345/419 |
| 2011/0187824 A1 | 8/2011 | Hori | | |
| 2011/0205552 A1 | 8/2011 | Bendall et al. | | |
| 2011/0210961 A1 * | 9/2011 | Bendall | ................. | G06T 7/0004 345/419 |
| 2011/0221877 A1 * | 9/2011 | Hori | ................. | H04N 7/183 348/65 |
| 2011/0260033 A1 * | 10/2011 | Steffensen | ................. | G01C 15/002 250/203.1 |
| 2012/0069012 A1 | 3/2012 | Facchin et al. | | |
| 2012/0223937 A1 * | 9/2012 | Bendall | ................. | G01B 11/24 345/419 |
| 2012/0256901 A1 | 10/2012 | Bendall | | |
| 2012/0314058 A1 | 12/2012 | Bendall et al. | | |
| 2013/0287288 A1 * | 10/2013 | Bendall | ................. | G06T 7/0004 382/154 |

(56) References Cited

U.S. PATENT DOCUMENTS

| | | | |
|---|---|---|---|
| 2014/0005978 A1* | 1/2014 | Shimizu | G01B 21/20 702/167 |
| 2015/0170352 A1 | 6/2015 | Bendall | |
| 2015/0170412 A1* | 6/2015 | Bendall | G06T 17/00 382/119 |
| 2015/0187067 A1 | 7/2015 | Bendall et al. | |
| 2015/0196202 A1* | 7/2015 | Mercader | A61B 18/00 600/478 |
| 2015/0317816 A1 | 11/2015 | Bendall et al. | |
| 2015/0339817 A1* | 11/2015 | Kuriyama | G06T 1/0007 348/71 |
| 2016/0155015 A1* | 6/2016 | Bendall | G06T 7/001 382/199 |
| 2016/0171705 A1* | 6/2016 | Bendall | G01B 11/03 382/103 |
| 2016/0196643 A1* | 7/2016 | Bendall | G06T 7/0008 382/108 |

FOREIGN PATENT DOCUMENTS

| | | |
|---|---|---|
| EP | 00888522 A1 | 1/1999 |
| GB | 2328280 A | 2/1999 |
| GB | 2505926 A | 3/2014 |
| JP | 11213177 A | 8/1999 |
| JP | 2001149319 A | 6/2001 |
| JP | 2005331488 A | 12/2005 |
| JP | 2007029460 A | 2/2007 |
| JP | 3898945 B2 | 3/2007 |
| JP | 2009053147 A | 3/2009 |
| WO | WO-2006056614 A1 | 6/2006 |
| WO | WO-2010107434 A1 | 9/2010 |

OTHER PUBLICATIONS

Cobzas et al. "A Panoramic Model for Remote Robot Environment Mapping and Predictive Display", Published 2005.

Search Report and Written Opinion from EP Application No. 12157924.7 dated Jun. 22, 2012.

Miniaturized three-dimensional endoscopic imaging system based on active sterovision, Authors: Manhong Chan; Wumei Lin; Changehe Zhou; Qu Jianan Y, Applied Optics ISSN 003-6935 Coden Apopai, 2003, vol. 42, n10, pp. 1888-1898 (11 page article).

U.S. Appl. No. 14/660,464, filed Mar. 17, 2015, Clark Alexander Bendall et al.

U.S. Appl. No. 14/108,976, filed Dec. 17, 2013, Clark Alexander Bendall.

U.S. Appl. No. 14/512,835, filed Oct. 13, 2014, Clark Alexander Bendall et al.

U.S. Appl. No. 15/018,587, filed Feb. 8, 2016, Clark Alexander Bendall.

U.S. Appl. No. 15/018,628, filed Feb. 8, 2016, Clark Alexander Bendall.

U.S. Appl. No. 14/753,604, filed Jun. 29, 2015, Clark Alexander Bendall et al.

U.S. Appl. No. 13/892,794, filed May 13, 2013, Clark Alexander Bendall et al.

U.S. Appl. No. 12/713,609, filed Feb. 26, 2010, Clark Alexander Bendall et al.

U.S. Appl. No. 13/040,678, filed Mar. 4, 2011, Clark Alexander Bendall.

Unofficial English translation of Office Action and Search Report issued in connection with related CN Application No. 201210063764.6 dated Sep. 2, 2015.

Unofficial English translation of Office Action issued in connection with related JP Application No. 2012-044901 dated Feb. 2, 2016.

Unofficial English translation of Office Action and Search Report issued in connection with related CN Application No. 201210063764.6 dated Apr. 18, 2016.

A International Search Report and Written Opinion issued in connection with related Application No. PCT/US2016/022312 dated Jul. 5, 2016.

\* cited by examiner

METHOD AND DEVICE FOR AUTOMATICALLY IDENTIFYING A POINT OF INTEREST IN A DEPTH MEASUREMENT ON A VIEWED OBJECT

CROSS-REFERENCE TO RELATED APPLICATIONS

This application is a Continuation-in-Part of, and claims priority to, U.S. patent application Ser. No. 14/108,976, filed Dec. 17, 2013, and entitled METHOD AND DEVICE FOR AUTOMATICALLY IDENTIFYING THE DEEPEST POINT ON THE SURFACE OF AN ANOMALY, the entirety of which is incorporated herein by reference.

BACKGROUND

The subject matter disclosed herein relates to a method and device for automatically identifying a point of interest in a depth measurement on a viewed object using a video inspection device.

Video inspection devices, such as video endoscopes or borescopes, can be used to take depth measurements on an object (e.g., lowest points in anomalies such as pits or dents, heights of welds, measurements of offsets or clearances between surfaces, etc.). In many instances, the surface of the object is inaccessible and cannot be viewed without the use of the video inspection device. For example, a video inspection device can be used to inspect the surface of a blade of a turbine engine on an aircraft or power generation unit to identify any anomalies to determine if any repair or further maintenance is required. In order to make that assessment, it is often necessary to obtain highly accurate-dimensional measurements of the surface to verify that the anomaly does not fall outside an operational limit or required specification for that object.

A video inspection device can be used to obtain and display a two-dimensional image of the surface of a viewed object to determine the depth measurement. This two-dimensional image of the surface can be used to generate three-dimensional data of the surface that provides the three-dimensional coordinates (e.g., (x, y, z)) of a plurality of points on the surface. In some video inspection devices, a depth measurement is determined by placing three cursors one at a time on a the surface of the object to establish a reference plane and then a fourth cursor at a point not on the plane to determine the perpendicular distance between the reference surface and the surface at the fourth point. Accordingly, the user has to move the fourth cursor around to find the point of interest on the surface to measure, e.g., the deepest point, the highest point, or the smallest clearance distance. This process can be time consuming and may not always result in the point of interest being identified in a depth measurement.

SUMMARY

A method and device for automatically identifying a point of interest in a depth measurement on a viewed object using a video inspection device is disclosed. The video inspection device determines the three-dimensional coordinates in a region of interest on the viewed object and analyzes those surface points to determine the desired measurement application (e.g., determining the deepest point, the highest point, or the clearance between two surfaces). Based on the desired measurement application, the video inspection device automatically identifies the point of interest on the viewed object and places a cursor at that location. An advantage that may be realized in the practice of some disclosed embodiments is that the time to perform the depth measurement is reduced and the accuracy of the measurement is improved since the user does not need to manually identify the point of interest for a particular measurement application.

In one embodiment, a method for automatically identifying a point of interest in a depth measurement of a viewed object is disclosed. The method comprises the steps of displaying on a monitor an image of the viewed object, determining the three-dimensional coordinates of a plurality of points on a surface of the viewed object using a central processor unit, determining a reference surface using the central processor unit, determining at least one region of interest that includes a plurality of points on the surface of the viewed object using a central processor unit, determining a distance between each of the plurality of points on the surface of the viewed object in the at least one region of interest and the reference surface using a central processor unit, and determining the point of interest as the point on the surface of the viewed object in the at least one region of interest having the greatest distance from the reference surface using a central processor unit.

In another embodiment, a method for automatically identifying a point of interest in a depth measurement of a viewed object having a first surface and a second surface that have a gap between them and are not parallel to each other is disclosed. The method comprises the steps of displaying on a monitor an image of the viewed object, determining the three-dimensional coordinates of a plurality of points on the first surface and the second surface of the viewed object using a central processor unit, determining a reference surface on the first surface of the viewed object using the central processor unit, determining at least one region of interest that includes a plurality of points on the second surface of the viewed object using a central processor unit, determining a distance between each of the plurality of points on the second surface of the viewed object in the at least one region of interest and the reference surface using a central processor unit, and determining the point of interest as a point on an edge of the second surface of the viewed object using a central processor unit.

In yet another embodiment, the a method for automatically identifying a point of interest in a depth measurement of a viewed object is disclosed. The method comprises the steps of displaying on a monitor an image of the viewed object, determining the three-dimensional coordinates of a plurality of points on a surface of the viewed object using a central processor unit, determining a reference surface using the central processor unit, determining at least one region of interest that includes a plurality of points on the surface of the viewed object using a central processor unit, determining a distance between each of the plurality of points on the surface of the viewed object in the at least one region of interest and the reference surface using a central processor unit, and determining the point of interest as the point on the surface of the viewed object in the at least one region of interest based on the distance between each of the plurality of points on the surface of the viewed object in the at least one region of interest and the reference surface using a central processor unit.

The above embodiments are exemplary only. Other embodiments are within the scope of the disclosed subject matter.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the disclosed subject matter encompasses other embodiments as well. The drawings are not necessarily to scale, emphasis generally being placed upon illustrating the features of certain embodiments of the invention. In the drawings, like numerals are used to indicate like parts throughout the various views.

DETAILED DESCRIPTION

Embodiments of the disclosed subject matter provide techniques for automatically identifying a point of interest in a depth measurement on a viewed object using a video inspection device. In one embodiment, the video inspect device determines the three-dimensional coordinates in a region of interest on the viewed object and analyzes those surface points to determine the desired measurement application (e.g., determining the deepest point, the highest point, or the clearance between two surfaces). Based on the desired measurement application, the video inspection device automatically identifies the point of interest on the viewed object and places a cursor at that location. Other embodiments are within the scope of the disclosed subject matter.

Figure 1:
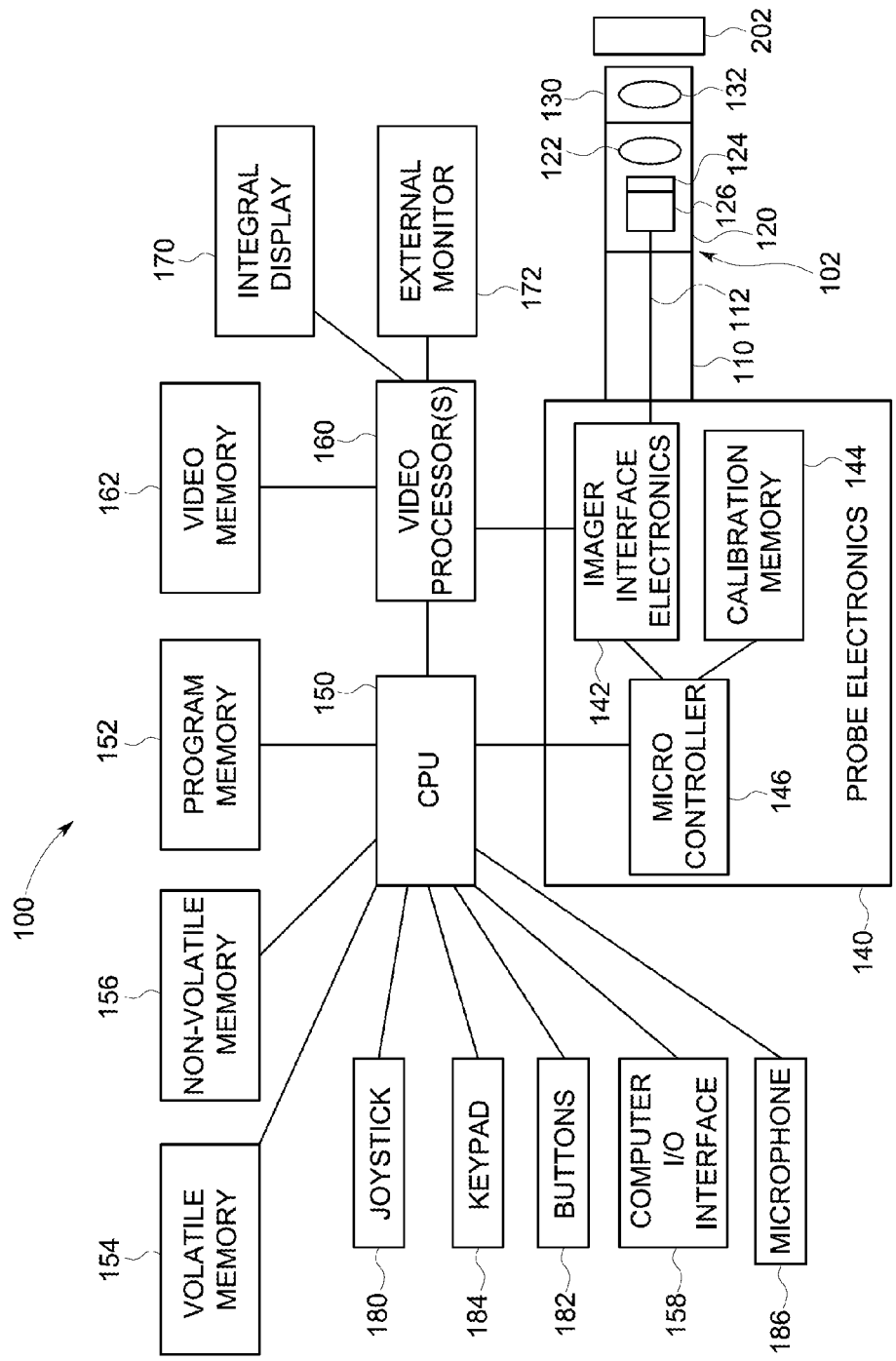
FIG. 1 is a block diagram of an exemplary video inspection device.

FIG. 1 is a block diagram of an exemplary video inspection device 100. It will be understood that the video inspection device 100 shown in FIG. 1 is exemplary and that the scope of the invention is not limited to any particular video inspection device 100 or any particular configuration of components within a video inspection device 100.

Video inspection device 100 can include an elongated probe 102 comprising an insertion tube 110 and a head assembly 120 disposed at the distal end of the insertion tube 110. Insertion tube 110 can be a flexible, tubular section through which all interconnects between the head assembly 120 and probe electronics 140 are passed. Head assembly 120 can include probe optics 122 for guiding and focusing light from the viewed object 202 onto an imager 124. The probe optics 122 can comprise, e.g., a lens singlet or a lens having multiple components. The imager 124 can be a solid state CCD or CMOS image sensor for obtaining an image of the viewed object 202.

A detachable tip or adaptor 130 can be placed on the distal end of the head assembly 120. The detachable tip 130 can include tip viewing optics 132 (e.g., lenses, windows, or apertures) that work in conjunction with the probe optics 122 to guide and focus light from the viewed object 202 onto an imager 124. The detachable tip 130 can also include illumination LEDs (not shown) if the source of light for the video inspection device 100 emanates from the tip 130 or a light passing element (not shown) for passing light from the probe 102 to the viewed object 202. The tip 130 can also provide the ability for side viewing by including a waveguide (e.g., a prism) to turn the camera view and light output to the side. The tip 130 may also provide stereoscopic optics or structured-light projecting elements for use in determining three-dimensional data of the viewed surface. The elements that can be included in the tip 130 can also be included in the probe 102 itself.

The imager 124 can include a plurality of pixels formed in a plurality of rows and columns and can generate image signals in the form of analog voltages representative of light incident on each pixel of the imager 124. The image signals can be propagated through imager hybrid 126, which provides electronics for signal buffering and conditioning, to an imager harness 112, which provides wires for control and video signals between the imager hybrid 126 and the imager interface electronics 142. The imager interface electronics 142 can include power supplies, a timing generator for generating imager clock signals, an analog front end for digitizing the imager video output signal, and a digital signal processor for processing the digitized imager video data into a more useful video format.

The imager interface electronics 142 are part of the probe electronics 140, which provide a collection of functions for operating the video inspection device 10. The probe electronics 140 can also include a calibration memory 144, which stores the calibration data for the probe 102 and/or tip 130. A microcontroller 146 can also be included in the probe electronics 140 for communicating with the imager interface electronics 142 to determine and set gain and exposure settings, storing and reading calibration data from the calibration memory 144, controlling the light delivered to the viewed object 202, and communicating with a central processor unit (CPU) 150 of the video inspection device 100.

In addition to communicating with the microcontroller 146, the imager interface electronics 142 can also communicate with one or more video processors 160. The video processor 160 can receive a video signal from the imager interface electronics 142 and output signals to various monitors 170, 172, including an integral display 170 or an external monitor 172. The integral display 170 can be an LCD screen built into the video inspection device 100 for displaying various images or data (e.g., the image of the viewed object 202, menus, cursors, measurement results) to an inspector. The external monitor 172 can be a video monitor or computer-type monitor connected to the video inspection device 100 for displaying various images or data.

The video processor 160 can provide/receive commands, status information, streaming video, still video images, and graphical overlays to/from the CPU 150 and may be comprised of FPGAs, DSPs, or other processing elements which provide functions such as image capture, image enhancement, graphical overlay merging, distortion correction, frame averaging, scaling, digital zooming, overlaying, merging, flipping, motion detection, and video format conversion and compression.

The CPU 150 can be used to manage the user interface by receiving input via a joystick 180, buttons 182, keypad 184, and/or microphone 186, in addition to providing a host of other functions, including image, video, and audio storage and recall functions, system control, and measurement processing. The joystick 180 can be manipulated by the user to perform such operations as menu selection, cursor movement, slider adjustment, and articulation control of the probe 102, and may include a push-button function. The buttons 182 and/or keypad 184 also can be used for menu selection and providing user commands to the CPU 150 (e.g., freezing or saving a still image). The microphone 186 can be used by the inspector to provide voice instructions to freeze or save a still image.

The video processor 160 can also communicate with video memory 162, which is used by the video processor 160 for frame buffering and temporary holding of data during processing. The CPU 150 can also communicate with CPU program memory 152 for storage of programs executed by the CPU 150. In addition, the CPU 150 can be in communication with volatile memory 154 (e.g., RAM), and non-volatile memory 156 (e.g., flash memory device, a hard drive, a DVD, or an EPROM memory device). The non-volatile memory 156 is the primary storage for streaming video and still images.

The CPU 150 can also be in communication with a computer I/O interface 158, which provides various interfaces to peripheral devices and networks, such as USB, Firewire, Ethernet, audio I/O, and wireless transceivers. This computer I/O interface 158 can be used to save, recall, transmit, and/or receive still images, streaming video, or audio. For example, a USB "thumb drive" or CompactFlash memory card can be plugged into computer I/O interface 158. In addition, the video inspection device 100 can be configured to send frames of image data or streaming video data to an external computer or server. The video inspection device 100 can incorporate a TCP/IP communication protocol suite and can be incorporated in a wide area network including a plurality of local and remote computers, each of the computers also incorporating a TCP/IP communication protocol suite. With incorporation of TCP/IP protocol suite, the video inspection device 100 incorporates several transport layer protocols including TCP and UDP and several different layer protocols including HTTP and FTP.

It will be understood that, while certain components have been shown as a single component (e.g., CPU 150) in FIG. 1, multiple separate components can be used to perform the functions of the CPU 150.

Figure 2:
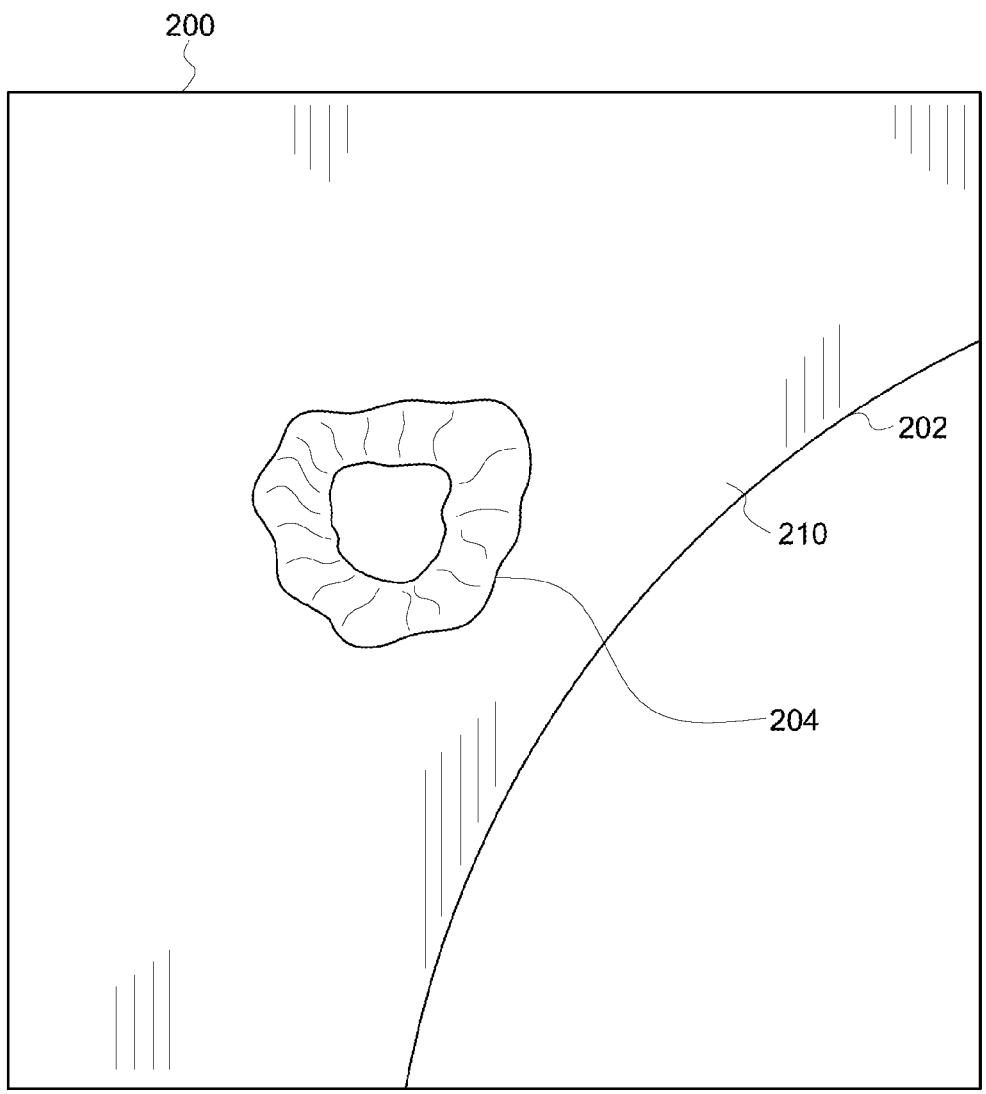
FIG. 2 is an exemplary image obtained by the video inspection device of the object surface of a viewed object having an anomaly in an exemplary embodiment.

FIG. 2 is an exemplary image 200 obtained by the video inspection device 100 of the object surface 210 of a viewed object 202 having an anomaly 204 in an exemplary embodiment of the invention. In this example, the anomaly 204 is shown as a dent, where material has been removed from the object surface 210 of the viewed object 202 in the anomaly 204 by damage or wear. It will be understood that the anomaly 204 shown in this exemplary embodiment is just an example and that the inventive method applies to other types of irregularities (e.g., cracks, corrosion pitting, coating loss, surface deposits, etc.), surface features (e.g., welds), or clearances between surfaces (e.g., tip to shroud clearances). Once the image 200 is obtained, and the anomaly 204 is identified, the image 200 can be used to determine the dimensions of the anomaly 204 (e.g., height or depth, length, width, area, volume, point to line, profile slice, etc.). In one embodiment, the image 200 used can be a two-dimensional image 200 of the object surface 210 of the viewed object 202, including the anomaly 204.

Figure 3:
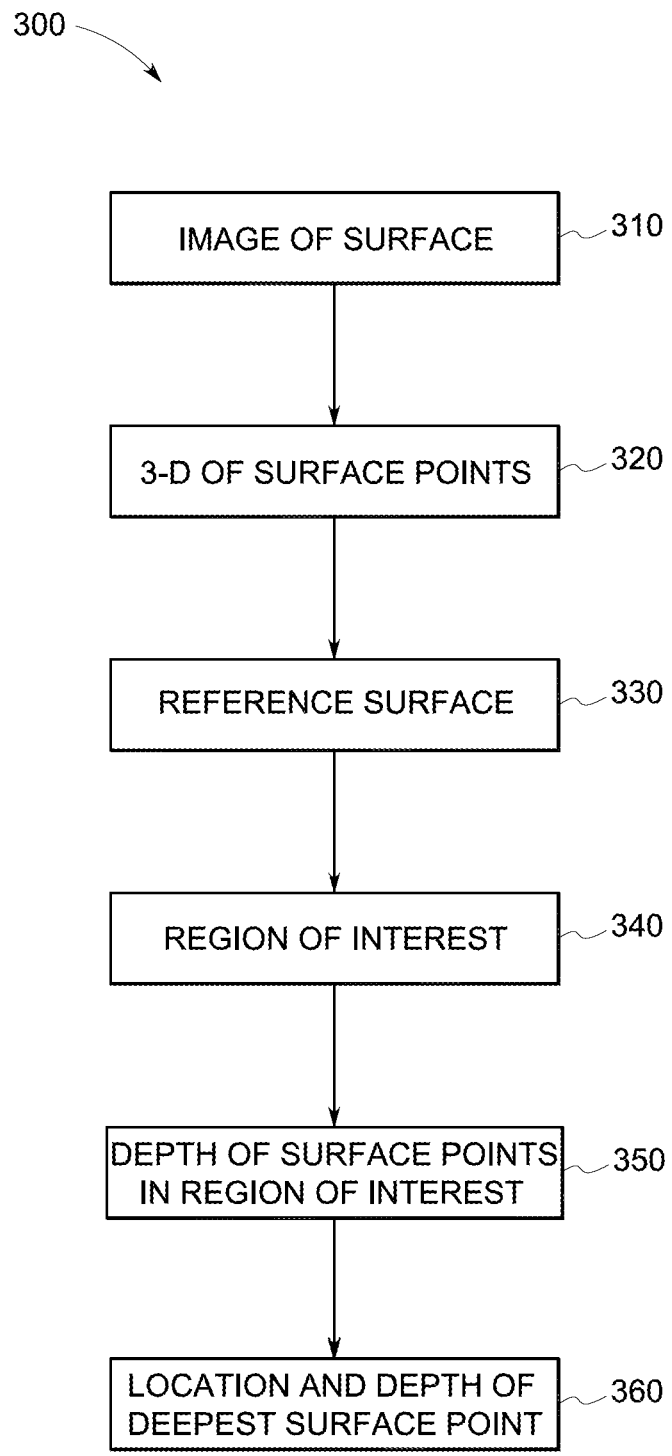
FIG. 3 is a flow diagram of an exemplary method for automatically identifying the point of interest on the surface of an anomaly on a viewed object shown in the image of FIG. 2 in an exemplary embodiment.

FIG. 3 is a flow diagram of an exemplary method 300 for automatically identifying the point of interest (e.g., deepest point) on the object surface 210 of an anomaly 204 on a viewed object 202 shown in the image 200 of FIG. 2 in an exemplary embodiment of the invention. It will be understood that the steps described in the flow diagram of FIG. 3 can be performed in a different order than shown in the flow diagram and that not all of the steps are required for certain embodiments.

At step 310 of the exemplary method 300 (FIG. 3) and as shown in FIG. 2, the user can use the video inspection device 100 (e.g., the imager 124) to obtain at least one image 200 of the object surface 210 of a viewed object 202 having an anomaly 204 and display it on a video monitor (e.g., an integral display 170 or external monitor 172). In one embodiment, the image 200 can be displayed in a measurement mode of the video inspection device.

At step 320 of the exemplary method 300 (FIG. 3), the video inspection device 100 (e.g., the CPU 150) can determine the three-dimensional coordinates (e.g., (x, y, z)) of a plurality of surface points on the object surface 210 of the viewed object 202, including surface points of the anomaly 204. In one embodiment, the video inspection device can generate three-dimensional data from the image 200 in order to determine the three-dimensional coordinates. Several different existing techniques can be used to provide the three-dimensional coordinates of the surface points in the image 200 (FIG. 2) of the object surface 210 (e.g., stereo, scanning systems, stereo triangulation, structured light methods such as phase shift analysis, phase shift moiré, laser dot projection, etc.).

Most such techniques comprise the use of calibration data, which, among other things, includes optical characteristic data that is used to reduce errors in the three-dimensional coordinates that would otherwise be induced by optical distortions. With some techniques, the three-dimensional coordinates may be determined using one or more images captured in close time proximity that may include projected patterns and the like. It is to be understood that references to three-dimensional coordinates determined using image 200 may also comprise three-dimensional coordinates determined using one or a plurality of images 200 of the object surface 210 captured in close time proximity, and that the image 200 displayed to the user during the described operations may or may not actually be used in the determination of the three-dimensional coordinates.

Figure 4:
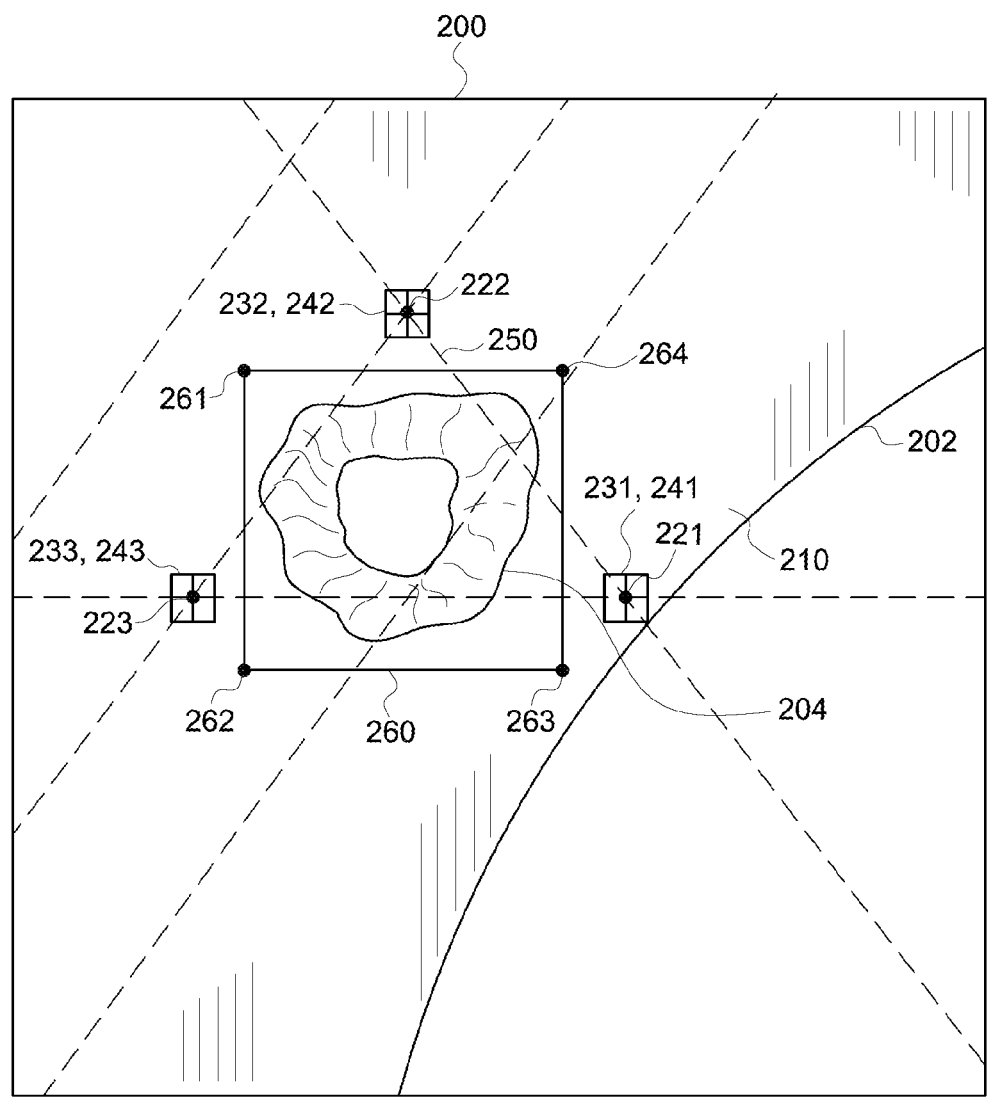
FIG. 4 illustrates an exemplary reference surface determined by the video inspection device.

At step 330 of the exemplary method 300 (FIG. 3), and as shown in FIG. 4, the video inspection device 100 (e.g., the CPU 150) can determine a reference surface 250. In some embodiments, the reference surface 250 can be flat, while in other embodiments the reference surface 250 can be curved. Similarly, in one embodiment, the reference surface 250 can be in the form of a plane, while in other embodiments, the reference surface 250 can be in the form of a different shape (e.g., cylinder, sphere, etc.). For example, a user can use the joystick 180 (or other pointing device (e.g., mouse, touch screen)) of the video inspection device 100 to select one or more reference surface points on the object surface 210 of the viewed object 202 proximate to the anomaly 204 to determine a reference surface.

In one embodiment and as shown in FIG. 4, a total of three reference surface points 221, 222, 223 are selected on the object surface 210 of the viewed object 202 proximate to the anomaly 204 to conduct a depth measurement of the anomaly 204, with the three reference surface points 221, 222, 223 selected on the object surface 210 proximate to the anomaly 204. In one embodiment, the plurality of reference surface points 221, 222, 223 on the object surface 210 of the viewed object 202 can be selected by placing reference surface cursors 231, 232, 233 (or other pointing devices) on pixels 241, 242, 243 of the image 200 corresponding to the plurality of reference surface points 221, 222, 223 on the object surface 210. In the exemplary depth measurement, the video inspection device 100 (e.g., the CPU 150) can determine the three-dimensional coordinates of each of the plurality of reference surface points 221, 222, 223.

The three-dimensional coordinates of three or more surface points proximate to one or more of the three reference surface points 221, 222, 223 selected on the object surface 210 proximate to the anomaly 204 can be used to determine a reference surface 250 (e.g., a plane). In one embodiment, the video inspection device 100 (e.g., the CPU 150) can perform a curve fitting of the three-dimensional coordinates of the three reference surface points 221, 222, 223 to determine an equation for the reference surface 250 (e.g., for a plane) having the following form:

$$k_{0RS}+k_{1RS1} \cdot x_{iRS}+k_{2RS} \cdot y_{iRS1}=z_{iRS} \quad (1)$$

where ($x_{iRS}$, $y_{iRS}$, $z_{iRS}$) are coordinates of any three-dimensional point on the defined reference surface 250 and $k_{0RS}$, $k_{1RS}$, and $k_{2RS}$ are coefficients obtained by a curve fitting of the three-dimensional coordinates.

It should be noted that a plurality of reference surface points (i.e., at least as many points as the number of k coefficients) are used to perform the curve fitting. The curve fitting finds the k coefficients that give the best fit to the points used (e.g., least squares approach). The k coefficients then define the plane or other reference surface 250 that approximates the three-dimensional points used. However, if more points are used in the curve fitting than the number of k coefficients, when you insert the x and y coordinates of the points used into the plane equation (1), the z results will generally not exactly match the z coordinates of the points due to noise and any deviation from a plane that may actually exist. Thus, the $x_{iRS1}$ and $y_{iRS1}$ can be any arbitrary values, and the resulting $Z_{iRS}$ tells you the z of the defined plane at $x_{iRS}$, $y_{iRS}$. Accordingly, coordinates shown in these equations can be for arbitrary points exactly on the defined surface, not necessarily the points used in the fitting to determine the k coefficients.

In other embodiments, there are only one or two reference surface points selected, prohibiting the use of curve fitting based only on the three-dimensional coordinates of those reference surface points since three points are needed to determine $k_{0RS}$, $k_{1RS}$, and $k_{2RS}$. In that case, the video inspection device 100 (e.g., the CPU 150) can identify a plurality of pixels proximate to each of the pixels of the image corresponding to a plurality of points on the object surface 210 proximate to the reference surface point(s), and determine the three-dimensional coordinates of the proximate point(s), enabling curve fitting to determine a reference surface 250.

While the exemplary reference surface 250 has been described as being determined based on reference surface points 221, 222, 223 selected by reference surface cursors 231, 232, 233, in other embodiments, the reference surface 250 can be formed by using a pointing device to place a reference surface shape 260 (e.g., circle, square, rectangle, triangle, etc.) proximate to anomaly 204 and using the reference surface points 261, 262, 263, 264 of the shape 260 to determine the reference surface 250. It will be understood that the reference surface points 261, 262, 263, 264 of the shape 260 can be points selected by the pointing device or be other points on or proximate to the perimeter of the shape that can be sized to enclose the anomaly 204.

Figure 5:
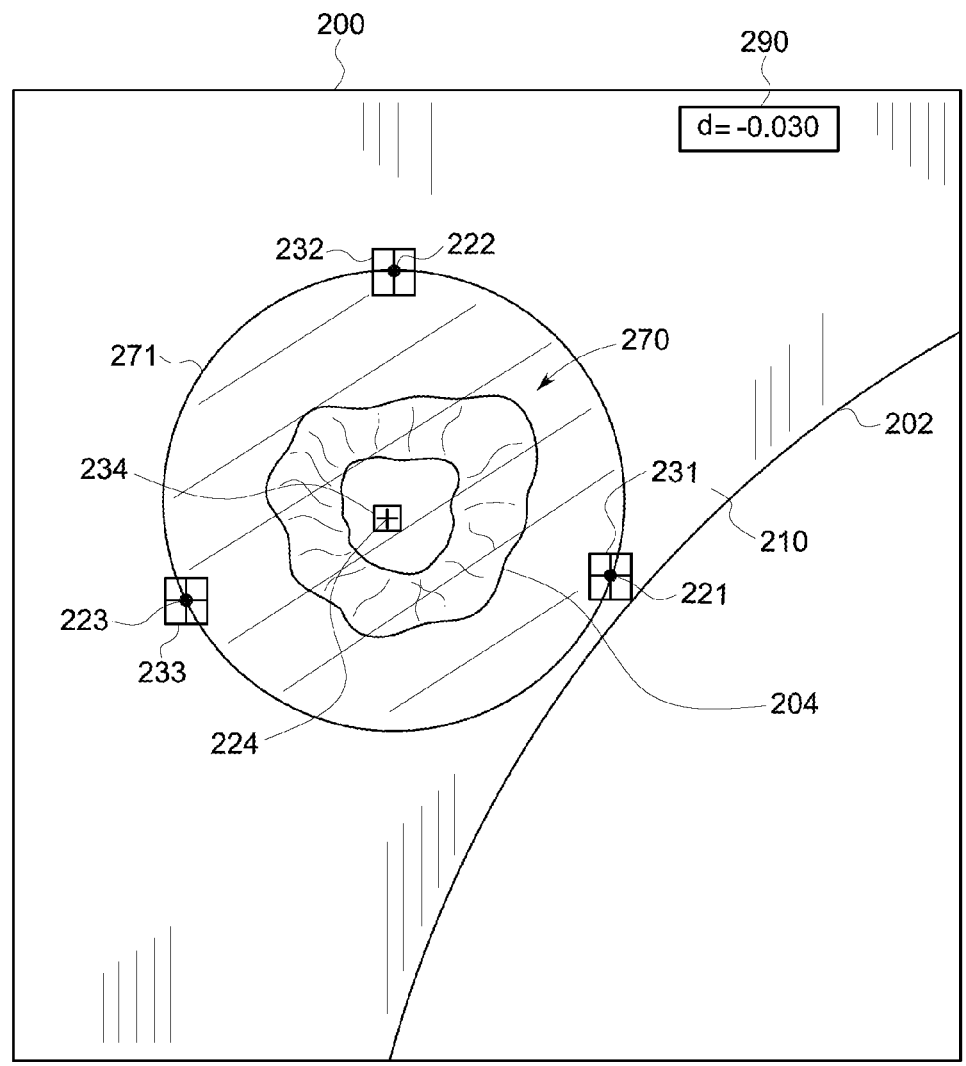
FIG. 5 illustrates an exemplary region of interest determined by the video inspection device.

At step 340 of the exemplary method 300 (FIG. 3), and as shown in FIG. 5, the video inspection device 100 (e.g., the CPU 150) determines a region of interest 270 proximate to the anomaly 204 based on the reference surface points of the reference surface 250. The region of interest 270 includes a plurality of surface points of the anomaly 204. In one embodiment, a region of interest 270 is formed by forming a region of interest shape 271 (e.g., a circle) based on two or more of the reference surface points 221, 222, 223. In another embodiment, the region of interest 270 can be determined by forming a cylinder perpendicular to the reference surface 260 and passing it through or proximate to two or more of the reference surface points 221, 222, 223. Referring again to FIG. 4, a region of interest could be formed within the reference surface shape 260 and reference surface points 261, 262, 263, 264.

Figure 6:
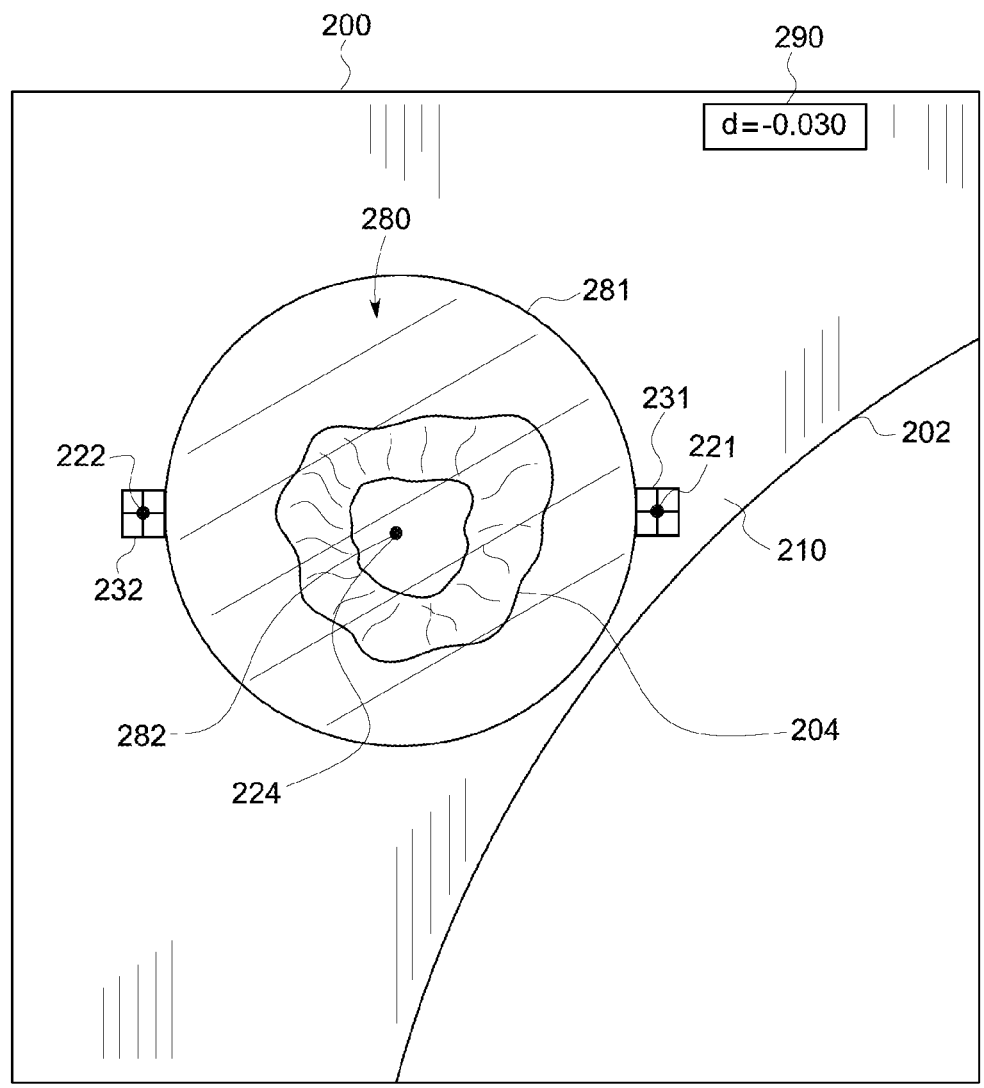
FIG. 6 illustrates another exemplary region of interest determined by the video inspection device.

Although the exemplary region of interest shape 271 in FIG. 5 is formed by passing through the reference surface points 221, 222, 223, in another embodiment, a smaller diameter reference surface shape can be formed by passing only proximate to the reference surface points. For example, as shown in FIG. 6, a region of interest 280 is formed by passing a region of interest shape 281 (e.g., a circle) proximate to two of the reference surface points 221, 222, where the diameter of the circle 281 is smaller than the distance between the two reference surface points 221, 222. It will be understood that region of interest shapes 271, 281 and the regions of interest 270, 280 may or may not be displayed on the image 200.

After the region of interest 270, 280 is determined, at step 350 of the exemplary method 300 (FIG. 3), the video inspection device 100 (e.g., the CPU 150) determines the distance (i.e., depth) from each of the plurality of surface points in the region of interest to the reference surface 250. In one embodiment, the video inspection device 100 (e.g., the CPU 150) determines the distance of a line extending between the reference surface 250 and each of the plurality of surface points in the region of interest 270, 280, wherein the line perpendicularly intersects the reference surface 250.

At step 360 of the exemplary method 300 (FIG. 3), the video inspection device determines the location of the deepest surface point 224 in the region of interest 270, 280 by determining the surface point that is furthest from the reference surface 250 (e.g., selecting the surface point with the longest line extending to the reference surface 250). It will be understood that, as used herein, the "deepest point" or "deepest surface point" can be a furthest point (i.e., lowest point) that is recessed relative to the reference surface 250 or a furthest point (i.e., highest point) that is protruding from the reference surface 250. The video inspection device 100 can identify the deepest surface point 224 in the region of interest 270, 280 on the image by displaying, e.g., a cursor 234 (FIG. 5) or other graphic identifier 282 (FIG. 6) on the deepest surface point 224. In addition and as shown in FIGS. 5 and 6, the video inspection device 100 can display the depth 290 (in inches or millimeters) of the deepest surface point 224 in the region of interest 270, 280 on the image 200 (i.e., the length of the perpendicular line extending from the deepest surface point 224 to the reference surface 250. By automatically displaying the cursor 234 or other graphic identifier 282 (FIG. 6) at the deepest surface point 224 in the region of interest 270, 280, the video inspection device 100 reduces the time required to perform the depth measurement and improves the accuracy of the depth measurement since the user does not need to manually identify the deepest surface point 224 in the anomaly 204.

Once the cursor 234 has been displayed at the deepest surface point 224 in the region of interest 270, 280, the user can select that point to take and save a depth measurement. The user can also move the cursor 234 within the region of interest 270, 280 to determine the depth of other surface points in the region of interest 270, 280. In one embodiment, the video inspection device 100 (e.g., CPU 150) can monitor the movement of the cursor 234 and detect when the cursor 234 has stopped moving. When the cursor 234 stops moving for a predetermined amount of time (e.g., 1 second), the video inspection device 100 (e.g., the CPU 150) can determine the deepest surface point proximate to the cursor 234 (e.g., a predetermined circle centered around the cursor 234) and automatically move the cursor 234 to that position.

If the user moves one or more of the reference surface cursors 231, 232, 233 (or other pointing devices) without manually adjusting the automatically placed cursor 234, cursor 234 is automatically repositioned based on the new region or interest 270 based on the new locations of the reference surface cursors 231, 232, 233. If the user moves one or more of the reference surface cursors 231, 232, 233 (or other pointing devices) after manually adjusting the automatically placed cursor 234, cursor 234 is not automatically repositioned based on the new region or interest 270 based on the new locations of the reference surface cursors 231, 232, 233. Accordingly, applications that are not supported for automatic placement are still supported for manual placement of the point of interest cursor 234.

Figure 7:
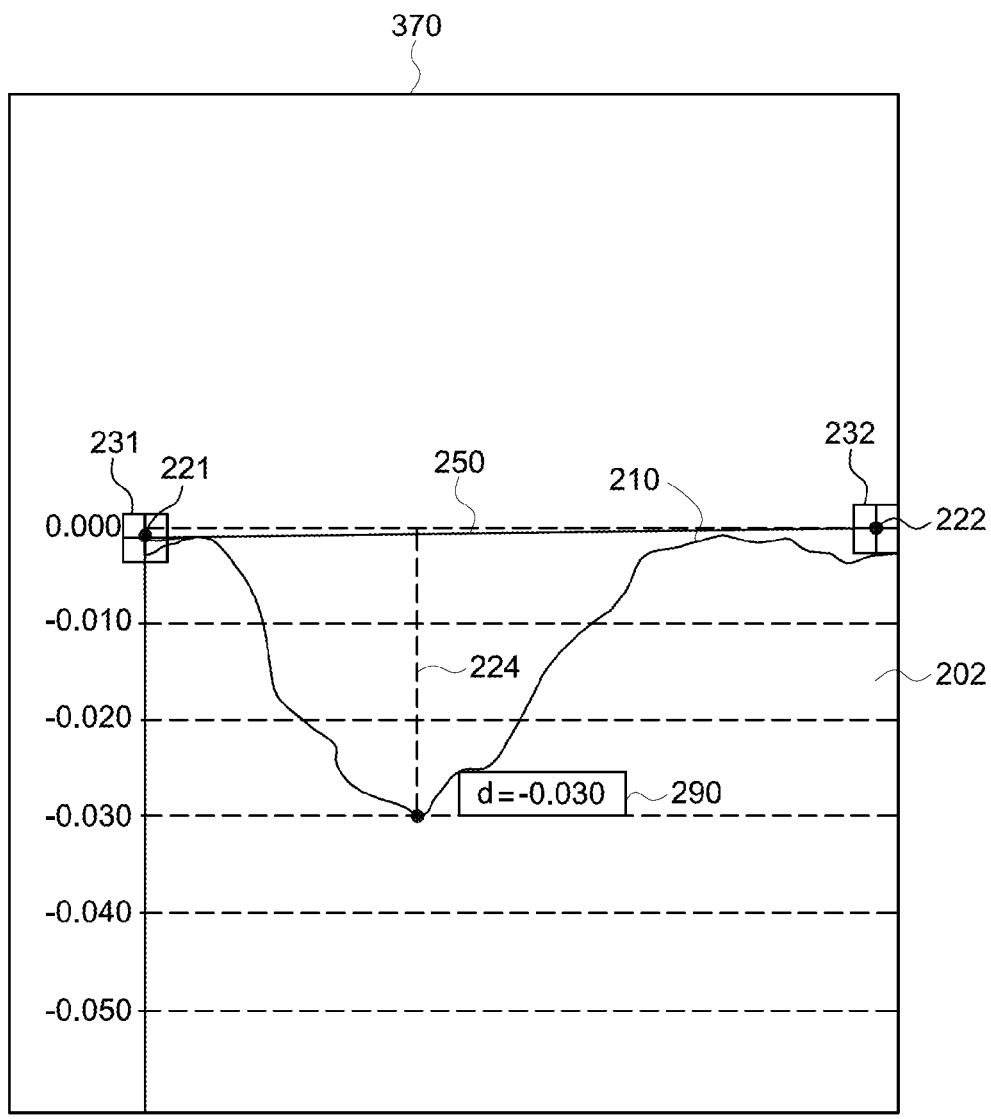
FIG. 7 is a graphical representation of an exemplary profile of the object surface of the viewed object shown in the image of FIG. 1 in an exemplary embodiment.

FIG. 7 is a graphical representation of an exemplary profile 370 of the object surface 210 of the viewed object 202 shown in the image 200 of FIG. 1. In this exemplary profile 370, the reference surface 250 is shown extending between two reference surface points 221, 222 and their respective reference surface cursors 231, 232. The location and depth 290 of the deepest surface point 224 in the region of interest is also shown in the graphical representation. In another embodiment, a point cloud view can also be used to show the deepest surface point 224.

Figure 8:
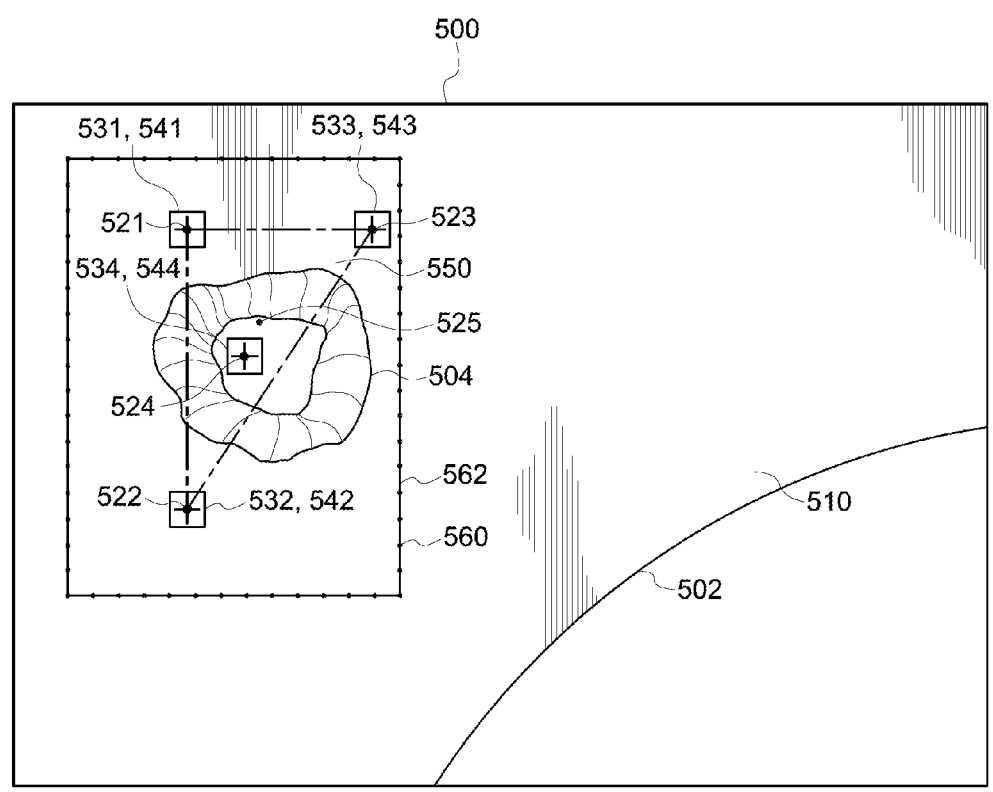
FIG. 8 is another image obtained by the video inspection device of the surface of a viewed object having an anomaly in an exemplary embodiment.

FIG. 8 is another image 500 obtained by the video inspection device 100 of the object surface 510 of a viewed object 502 having an anomaly 504 in an exemplary embodiment of the invention. Once again, in this example, the anomaly 504 is shown as a dent, where material has been removed from the object surface 510 of the viewed object 502 in the anomaly 504 by damage or wear. It will be understood that the anomaly 504 shown in this exemplary embodiment is just an example and that the inventive method applies to other types of irregularities (e.g., cracks, corrosion pitting, coating loss, surface deposits, etc.), surface features (e.g., welds), or clearances between surfaces (e.g., tip to shroud clearances). Once the image 500 is obtained, and the anomaly 504 is identified, the image 500 can be used to determine the dimensions of the anomaly 504 (e.g., height or depth, length, width, area, volume, point to line, profile slice, etc.). In one embodiment, the image 500 used can be a two-dimensional image 500 of the object surface 510 of the viewed object 502, including the anomaly 504.

Figure 9:
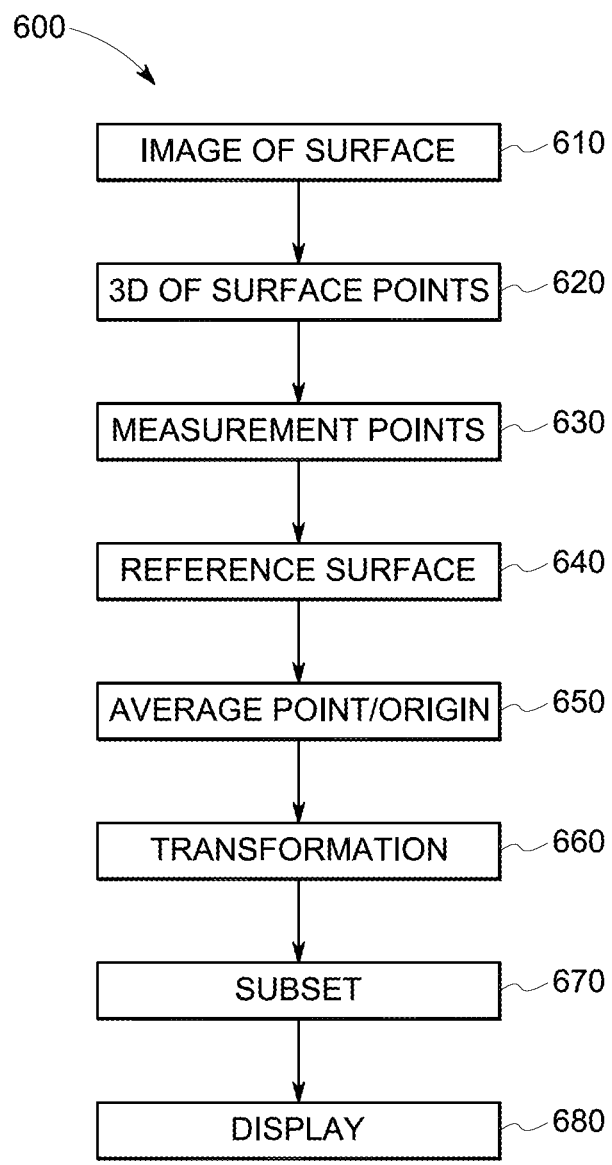
FIG. 9 is a flow diagram of a method for displaying three-dimensional data for inspection of the surface of the viewed object shown in the image of FIG. 8 in an exemplary embodiment.

FIG. 9 is a flow diagram of a method 600 for displaying three-dimensional data for inspection of the object surface 510 of the viewed object 502 shown in the image 500 of FIG. 8 in an exemplary embodiment of the invention. It will be understood that the steps described in the flow diagram of FIG. 9 can be performed in a different order than shown in the flow diagram and that not all of the steps are required for certain embodiments.

At step 610, and as shown in FIG. 8, the operator can use the video inspection device 100 to obtain an image 500 of the object surface 510 of a viewed object 502 having an anomaly 504 and display it on a video monitor (e.g., an integral display 170 or external monitor 172). In one embodiment, the image 500 can be displayed in a measurement mode of the video inspection device.

At step 620, the CPU 150 of the video inspection device 100 can determine the three-dimensional coordinates ($x_{iS1}$, $y_{iS1}$, $z_{iS1}$) in a first coordinate system of a plurality of surface points on the object surface 510 of the viewed object 502, including the anomaly 504. In one embodiment, the video inspection device can generate three-dimensional data from the image 500 in order to determine the three-dimensional coordinates. As discussed above, several different existing techniques can be used to provide the three-dimensional coordinates of the points on the image 500 of the object surface 510 (e.g., stereo, scanning systems, structured light methods such as phase shifting, phase shift moiré, laser dot projection, etc.).

At step 630, and as shown in FIG. 8, an operator can use the joystick 180 (or other pointing device (e.g., mouse, touch screen)) of the video inspection device 100 to select a plurality of measurement points on the object surface 510 of the viewed object 502 proximate the anomaly 504 to conduct a particular type of measurement. In one embodiment and as shown in FIG. 8, a total of three measurement points 521, 522, 523 are selected on the object surface 510 of the viewed object 502 proximate the anomaly 504 to conduct a depth measurement of the anomaly 504, and the fourth measurement point 524 automatically placed at the deepest point of the anomaly 504 as discussed above. In one embodiment, the plurality of measurement points 521, 522, 523 on the object surface 510 of the viewed object 502 can be selected by placing cursors 531, 532, 533 (or other pointing devices) on pixels 541, 542, 543 of the image 500 corresponding to the plurality of measurement points 521, 522, 523 on the object surface 510. A cursor 534 is automatically placed at the fourth measurement point 524 on a pixel 544 of the image 500 corresponding to the fourth measurement point 524. In the exemplary depth measurement, the video inspection device 100 can determine the three-dimensional coordinates in the first coordinate system of each of the plurality of measurement points 521, 522, 523, 524.

At step 640, and as shown in FIG. 8, the CPU 150 of the video inspection device 100 can determine a reference surface 550. In the exemplary depth measurement of the anomaly 504 shown in FIG. 8, the three-dimensional coordinates of three or more surface points proximate one or more of the three measurement points 521, 522, 523 selected on the object surface 510 proximate the anomaly 504 can be used to determine a reference surface 550 (e.g., a plane). In one embodiment, the video inspection device 100 can perform a curve fitting of the three-dimensional coordinates in the first coordinate system of the three measurement points 521, 522, 523 ($x_{iM1}$, $y_{iM1}$, $z_{iM1}$) to determine an equation for the reference surface 550 (e.g., for a plane) having the following form:

$$k_{ORS1} + k_{1RS1} x_{iRS1} + k_{2RS1} y_{iRS1} = z_{iRS1} \quad (2)$$

where ($x_{iRS1}$, $y_{iRS1}$, $z_{iRS1}$) are coordinates of any three-dimensional point in the first coordinate system on the defined reference surface 550 and $k_{ORS1}$, $k_{1RS1}$, and $k_{2RS1}$ are coefficients obtained by a curve fitting of the three-dimensional coordinates in the first coordinate system.

It should be noted that a plurality of measurement points (i.e., at least as many points as the number of k coefficients) are used to perform the curve fitting. The curve fitting finds the k coefficients that give the best fit to the points used (e.g., least squares approach). The k coefficients then define the plane or other reference surface 550 that approximates the three-dimensional points used. However, if more points are used in the curve fitting than the number of k coefficients, when you insert the x and y coordinates of the points used into the plane equation (2), the z results will generally not exactly match the z coordinates of the points due to noise and any deviation from a plane that may actually exist. Thus, the $x_{iRS1}$ and $y_{iRS1}$ can be any arbitrary values, and the resulting $z_{iRS1}$ tells you the z of the defined plane at $x_{iRS1}$, $y_{iRS1}$. Accordingly, coordinates shown in these equations can be for arbitrary points exactly on the defined surface, not necessarily the points used in the fitting to determine the k coefficients.

In another embodiment, there are only two measurement points selected for a particular measurement (e.g., length, profile), prohibiting the use of curve fitting based only on the three-dimensional coordinates of those two measurement points since three points are needed to determine $k_{ORS1}$, $k_{1RS1}$, and $k_{2RS1}$. In that case, the video inspection device 100 can identify a plurality of pixels proximate each of the pixels of the image corresponding to a plurality of points on the object surface 510 proximate each of the measurement points, and determine the three-dimensional coordinates of those points, enabling curve fitting to determine a reference surface 550.

In one embodiment and as shown in FIG. 8, the video inspection device 100 can determine the three-dimensional coordinates in the first coordinate system of a plurality of frame points 560 ($x_{iF1}$, $y_{iF1}$, $z_{iF1}$) forming a frame 562 (e.g., a rectangle) on the reference surface 550 around the anomaly 504 and the measurement points 521, 522, 523, 524, which can be used later to display the location of the reference surface 550.

Once the reference surface 550 is determined, in the exemplary embodiment shown in FIG. 8, the video inspection device 100 can conduct a measurement (e.g., depth) of the anomaly 504 by determining the distance between the fourth measurement point 524 at the deepest point of the anomaly 504 and the reference surface 550. The accuracy of this depth measurement is determined by the accuracy in selecting the plurality of measurement points 521, 522, 523 on the object surface 510 of the viewed object 502. In many instances as discussed previously, the contour of the anomaly 504 in the image 500 is difficult to assess from the two-dimensional image and may be too small or otherwise insufficient to reliably locate the plurality of measurement points 521, 522, 523. Accordingly, in many cases, an operator will want further detail in the area of the anomaly 504 to evaluate the accuracy of the location of these measurement points 521, 522, 523, 524. So while some video inspection devices 100 can provide a point cloud view of the full image 500, that view may not provide the required level of detail of the anomaly 504 as discussed previously. In order to provide a more meaningful view of the object surface 510 in the area around the measurement points 521, 522, 523, 524 than offered by a point cloud view of the three-dimensional data of the entire image 500, the inventive method creates a subset of the three-dimensional data in the region of interest.

At step 650, the CPU 150 of the video inspection device 100 can establish a second coordinate system different from the first coordinate system. In one embodiment, the second coordinate system can be based on the reference surface 550 and the plurality of measurement points 521, 522, 523, 524. The video inspection device 100 can assign the origin of the second coordinate system ($x_{O2}$, $y_{O2}$, $z_{O2}$)=(0, 0, 0) to be located proximate the average position 525 of the three-dimensional coordinates of points on the reference surface 550 corresponding to two or more of the plurality of measurement points 521, 522, 523, 524 on the object surface 510 (e.g., by projecting the measurement points 521, 522, 523, 524 onto the reference surface 550 and determining an average position 525 on the reference surface 550). In some cases, the three-dimensional coordinates of the points on the reference surface 550 corresponding to the measurement points 521, 522, 523 can be the same. However, in some circumstances, due to noise and/or small variations in the object surface 510, the measurement points 521, 522, 523 do not fall exactly on the reference surface 550, and therefore have different coordinates.

When determining points on the reference surface 550 that correspond to measurement points 521, 522, 523, 524 on the object surface 510, it is convenient to apply the concept of line directions, which convey the relative slopes of lines in the x, y, and z planes, and can be used to establish perpendicular or parallel lines. For a given line passing through two three-dimensional coordinates (x1, y1, z1) and (x2,y2,z2), the line directions (dx, dy, dz) may be defined as:

$$dx = x2 - x1 \quad (3)$$

$$dy = y2 - y1 \quad (4)$$

$$dz = z2 - z1 \quad (5)$$

Given a point on a line (x1, y1, z1) and the line's directions (dx, dy, dz), the line can be defined by:

$$\frac{(x - x1)}{dx} = \frac{(y - y1)}{dy} = \frac{(z - z1)}{dz} \quad (6)$$

Thus, given any one of an x, y, or z coordinate, the remaining two can be computed. Parallel lines have the same or linearly scaled line directions. Two lines having directions (dx1, dy1, dz1) and (dx2, dy2, dz2) are perpendicular if:

$$dx1 \cdot dx2 + dy1 \cdot dy2 + dz1 \cdot dz2 = 0 \quad (7)$$

The directions for all lines normal to a reference plane defined using equation (2) are given by:

$$dx_{RSN} = -k_{1RS} \quad (8)$$

$$dy_{RSN} = -k_{2RS} \quad (9)$$

$$dz_{RSN} = 1 \quad (10)$$

Based on equations (6) and (8) through (10), a line that is perpendicular to the reference surface 550 and passing through a surface point ($x_S$, $y_S$, $z_S$) can be defined as:

$$\frac{x - x_S}{-k_{1RS}} = \frac{y - y_S}{-k_{2RS}} = z - z_S \quad (11)$$

In one embodiment, the coordinates of a point on the reference surface 550 ($x_{iRS1}$, $y_{iRS1}$, $z_{iRS1}$) corresponding to a point on the object surface 510 ($x_{iS1}$, $y_{iS1}$, $z_{iS1}$) (e.g. three-dimensional coordinates in a first coordinate system of points on the reference surface 550 corresponding to the measurement points 521, 522, 523, 524), can be determined by defining a line normal to the reference surface 550 having directions given in equations (8)-(10) and passing through ($x_{iS1}$, $y_{iS1}$, $z_{iS1}$), and determining the coordinates of the intersection of that line with the reference surface 550. Thus, from equations (2) and (11):

$$z_{iRS} = \frac{(k_{1RS}^2 \cdot z_{iS1} + k_{1RS} \cdot x_{iS1} + k_{2RS}^2 \cdot z_{iS1} + k_{2RS} \cdot y_{iS1} + k_{ORS})}{(1 + k_{1RS}^2 + k_{2RS}^2)} \quad (12)$$

$$x_{iRS1} = k_{1RS1} \cdot (z_{iS1} - z_{iRS1}) + x_{iS1} \quad (13)$$

$$y_{iRS1} = k_{2RS} \cdot (z_{iS1} - z_{iRS1}) + y_{iS1} \quad (14)$$

In one embodiment, these steps (equations (3) through (14)) can be used to determine the three-dimensional coordinates of points on the reference surface 550 corresponding to the measurement points 521, 522, 523, 524. Then the average position 525 of these projected points of the measurement points on the reference surface 550 ($x_{M1avg}$, $y_{M1avg}$, $z_{M1avg}$) can be determined. The origin of the second coordinate system ($x_{O2}$, $y_{O2}$, $z_{O2}$)=(0, 0, 0) can then be assigned and located proximate the average position 525 ($x_{M1avg}$, $y_{M1avg}$, $z_{M1avg}$).

Locating the origin of the second coordinate system proximate the average position 525 in the area of the anomaly 504 with the z values being the perpendicular distance from each surface point to the reference surface 550 allows a point cloud view rotation to be about the center of the area of the anomaly 504 and permits any depth map color scale to indicate the height or depth of a surface point from the reference surface 550.

In order to take advantage of this second coordinate system, at step 660, the CPU 150 of the video inspection device 100 transforms the three-dimensional coordinates in the first coordinate system ($x_{i1}$, $y_{i1}$, $z_{i1}$) determined for various points (e.g., the plurality of surface points, the plurality of measurement points 521, 522, 523, 524, the points on the reference surface 550 including the frame points 560, etc.) to three-dimensional coordinates in the second coordinate system ($x_{i2}$, $y_{i2}$, $z_{i2}$).

In one embodiment, a coordinate transformation matrix ([T]) can be used to transform the coordinates according to the following:

$$([x_{i1}y_{i1}z_{i1}]-[x_{M1avg}y_{M1avg}z_{M1avg}])*[T]=[x_{i2}y_{i2}z_{i2}] \quad (15)$$

where [T] is a transformation matrix.

In non-matrix form, the three-dimensional coordinates in the second coordinate system can be determined by the following:

$$x_{i2}=(x_{i1}-x_{M1avg})*T_{00}+(y_{i1}-y_{M1avg})*T_{10}+(z_{i1}-z_{M1avg})*T_{20} \quad (16)$$

$$y_{i2}=(x_{i1}-x_{M1avg})*T_{01}+(y_{i1}-y_{M1avg})*T_{11}+(z_{i1}-z_{M1avg})*T_{21} \quad (17)$$

$$z_{i2}=(x_{i1}-x_{M1avg})*T_{02}+(y_{i1}-y_{M1avg})*T_{12}+(z_{i1}-z_{M1avg})*T_{22} \quad (18)$$

where the transformation matrix values are the line direction values of the new x, y, and z axes in the first coordinate system.

At step 670, the CPU 150 of the video inspection device 100 determines a subset of the plurality of surface points that are within a region of interest on the object surface 510 of the viewed object 502. In one embodiment, the region of interest can be a limited area on the object surface 510 of the viewed object 502 surrounding the plurality of measurement points 521, 522, 523, 524 to minimize the amount of three-dimensional data to be used in a point cloud view. For example, the region of interest can be defined by the frame 562. It will be understood that the step of determining of the subset 660 can take place before or after the transformation step 660. For example, if the determination of the subset at step 670 takes place after the transformation step 660, the video inspection device 100 may transform the coordinates for all surface points, including points that are outside the region of interest, before determining which of those points are in the region of interest. Alternatively, if the determination of the subset at step 670 takes place before the transformation step 660, the video inspection device 100 may only need to transform the coordinates for those surface points that are within the region of interest.

In one embodiment, the region of interest can be defined by determining the maximum distance ($d_{MAX}$) between each of the points on the reference surface 550 corresponding to the measurement points 521, 522, 523, 524 and the average position 525 of those points on the reference surface 550 (the origin of the second coordinate system ($x_{O2}$, $y_{O2}$, $z_{O2}$)=(0, 0, 0) if done after the transformation, or ($x_{M1avg}$, $y_{M1avg}$, $z_{M1avg}$) in the first coordinate system if done before the transformation). In one embodiment, the region of interest can include all surface points that have corresponding points on the reference surface 550 (i.e., when projected onto the reference surface) that are within a certain threshold distance ($d_{ROI}$) of the average position 525 of the measurement points 521, 522, 523, 524 on the reference surface 550 (e.g., less than the maximum distance ($d_{ROI}=d_{MAX}$) or less than a distance slightly greater (e.g. twenty percent greater) than the maximum distance ($d_{ROI}=1.2*d_{MAX}$)). For example, if the average position 525 in the second coordinate system is at ($x_{O2}$, $y_{O2}$, $z_{O2}$)=(0, 0, 0), the distance (d) from that position to a point on the reference surface 550 corresponding to a surface point ($x_{iRS2}$, $y_{iRS2}$, $z_{iRS2}$) is given by:

$$d_{iRS2}=\sqrt{(x_{iRS2}-x_{O2})^2+(y_{iRS2}-y_{O2})^2} \quad (19)$$

Similarly, if the average position 525 in the first coordinate system is at ($X_{M1avg}$, $y_{M1avg}$, $Z_{M1avg}$), the distance (d) from that position to a point on the reference surface 550 corresponding to a surface point ($x_{iRS1}$, $y_{iRS1}$, $z_{iRS1}$) is given by:

$$d_{iRS1}=\sqrt{(x_{iRS1}-x_{M1avg})^2+(y_{iRS1}-y_{M1avg})^2} \quad (20)$$

If a surface point has a distance value ($d_{iRS1}$ or $d_{iRS2}$) less than the region of interest threshold distance ($d_{ROI}$) and therefore in the region of interest, the video inspection device 100 can write the three-dimensional coordinates of that surface point and the pixel color corresponding to the depth of that surface point to a point cloud view file. In this exemplary embodiment, the region of interest is in the form of a cylinder that includes surface points falling within the radius of the cylinder. It will be understood that other shapes and methods for determining the region of interest can be used.

The region of interest can also be defined based upon the depth of the anomaly 504 on the object surface 510 of the viewed object 502 determined by the video inspection device 100 in the first coordinate system. For example, if the depth of the anomaly 504 was measured to be 0.005 inches (0.127 mm), the region of interest can be defined to include only those points having distances from the reference surface 550 (or z dimensions) within a certain range (±0.015 inches (0.381 mm)) based on the distance of one or more of the measurement points 521, 522, 523, 524 to the reference surface 550. If a surface point has a depth value inside the region of interest, the video inspection device 100 can write the three-dimensional coordinates of that surface point and the pixel color corresponding to the depth of that surface point to a point cloud view file. If a surface point has a depth value outside of the region of interest, the video inspection device 100 may not include that surface point in a point cloud view file.

Figure 10:
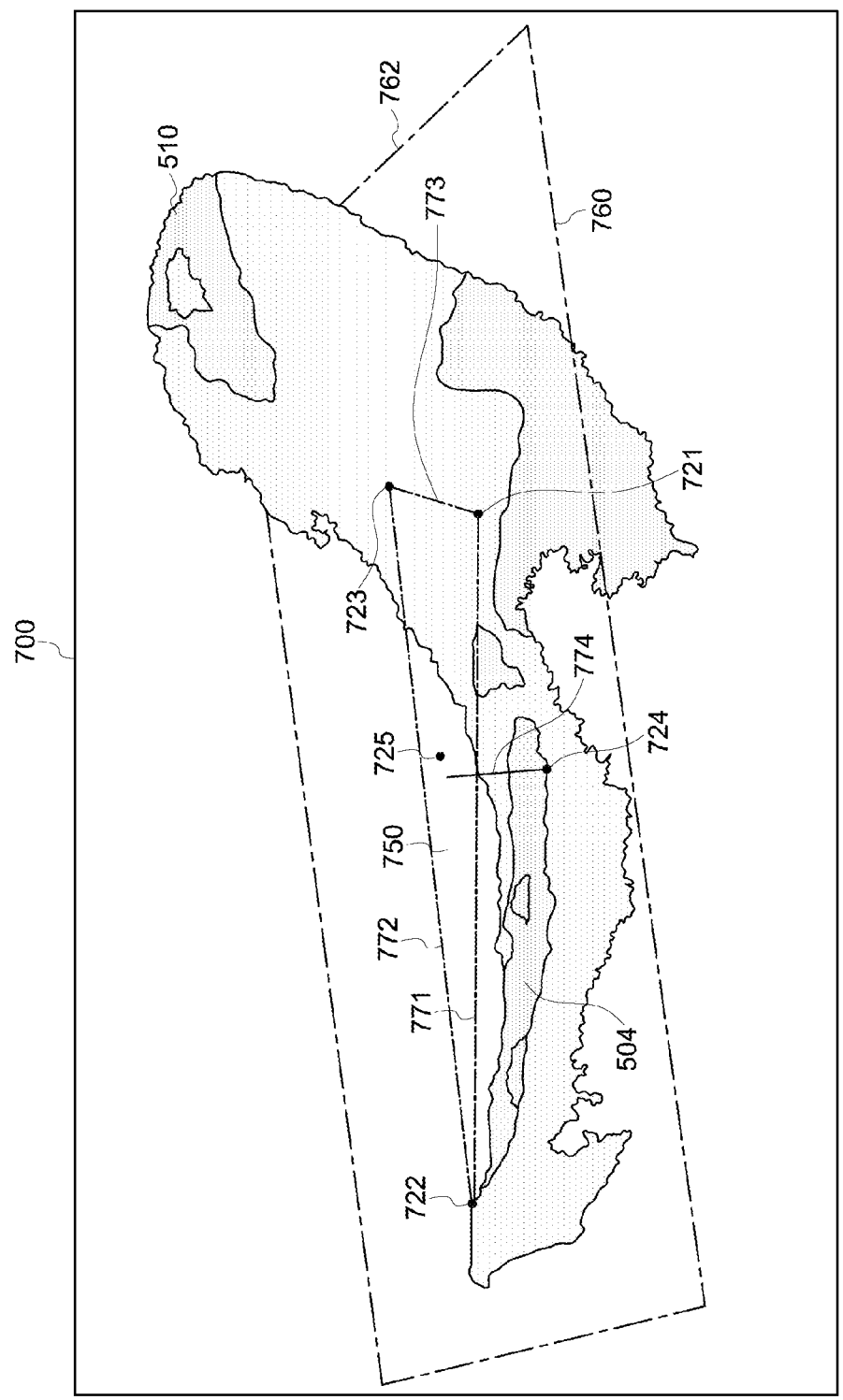
FIG. 10 is a display of a subset of a plurality of surface points in a point cloud view.

At step 680, and as shown in FIG. 10, the monitor 170, 172 of the video inspection device 100 can display a rendered three-dimensional view (e.g., a point cloud view) 700 of the subset of the plurality of surface points in the three-dimensional coordinates of the second coordinate system, having an origin 725 at the center of the view. In one embodiment (not shown), the display of the point cloud view 700 can include a color map to indicate the distance between each of the surface points and the reference surface 750 in the second coordinate system (e.g., a first point at a certain depth is shown in a shade of red corresponding that depth, a second point at a different depth is shown in a shade of green corresponding to that depth). The displayed point cloud view 700 can also include the location of the plurality of measurement points 721, 722, 723, 724. To assist the operator in viewing the point cloud view 700, the video inspection device 100 can also determine three-dimensional line points 771, 772, 773 along straight lines between two or more of the plurality of measurement points 721, 722, 723 in the three-dimensional coordinates of the second coordinate system, and display those line points 771, 772, 773 in the point cloud view 700. The point cloud view 700 can also include a depth line 774 from the measurement point 724 intended to be located at the deepest point of the anomaly 504 to the reference surface 750. In one embodiment, the video inspection device 100 can determine if the depth line 774 exceeds a tolerance specification or other threshold and provide a visual or audible indication or alarm of such an occurrence.

The displayed point cloud view 700 can also include a plurality of frame points 760 forming a frame 762 on the reference surface 750 in the second coordinate system to indicate the location of the reference surface 750. In another embodiment, the displayed point cloud view 700 can also include a scale indicating the perpendicular distance from the reference surface 750.

As shown in FIG. 10, by limiting the data in the point cloud view 700 to those points in the region of interest and allowing the view to be rotated about a point 725 in the center of the region of interest (e.g., at the origin), the operator can more easily analyze the anomaly 504 and determine if the depth measurement and placement of the measurement points 721, 722, 723, 724 was accurate. In one embodiment, the operator can alter the location of one or more of the measurement points 721, 722, 723, 724 in the point cloud view 700 if correction is required. Alternatively, if correction is required, the operator can return to the two-dimensional image 500 of FIG. 8 and reselect one or more of the measurement points 521, 522, 523, 524, and repeat the process.

In another embodiment, the monitor 170, 172 of the video inspection device 100 can display a rendered three-dimensional view 700 of the subset of the plurality of surface points in the three-dimensional coordinates of the first coordinate system without ever conducting a transformation of coordinates. In this embodiment, the point cloud view 700 based on the original coordinates can also include the various features described above to assist the operator, including displaying a color map, the location of the plurality of measurement points, three-dimensional line points, depth lines, frames, or scales.

Referring again to FIGS. 1-8 and the description of the method for automatically identifying a point of interest (e.g., the deepest point 224 (FIG. 5), 524 (FIG. 8)) in a depth measurement on a viewed object 202,502, in one embodiment, the video inspection device 100 (e.g., the CPU 150) can analyze the two-dimensional and/or three-dimensional data (e.g., three dimensional coordinates) of the surface points within the region of interest 270, 562 to determine what particular depth measurement application (e.g., deepest point or highest point) the user is performing prior to automatically identifying the point of interest 224, 524 and automatically placing a cursor 234, 534 at that location (FIGS. 5, 8.) For example, as shown in FIGS. 5 and 8, the region of interest can include all of the surface points on the viewed object 202, 502 whose normal line projections to the reference surface 250, 550 fall within the polygon formed by the three reference surface cursors 231, 232, 233, 531, 532, 533. In another embodiment, the region of interest can include pixels of the two-dimensional image 200, 500 that fall within the polygon formed by the three reference surface cursors 231, 232, 233, 531, 532, 533.

In one embodiment, a coordinate transformation can be performed such that the transformed z value for all points on the reference surface 270, 550 is z=0. Depending on the viewing perspective of the viewed object 202, 502 (e.g., viewing from above and looking down on the viewed object 202, 502), in the transformed coordinate system, the three-dimensional coordinates of any surface point lower than (or below) the reference surface 250, 550 has a negative z value and the three-dimensional coordinates of any surface point higher than (or above) the reference surface 550 has a positive z value. The video inspection device 100 (e.g., the CPU 150) can determine the distances from each of the surface points in the region of interest to the reference surface 250, 550 and identify the surface point in the region of interest having the largest absolute value for z as the surface point that is furthest from the reference surface 250, 550 (i.e., having the greatest distance from the reference surface 250, 550) and therefore assumed to be the point of interest and automatically place the fourth cursor 234, 534 at that location (FIGS. 5, 8). If the transformed actual value of the z value is negative, the point of interest is the deepest or lowest point, and if the transformed actual value of the z value is positive, the point of interest is the highest point.

In one embodiment, the video inspection device 100 (e.g., the CPU 150) can compare the largest absolute value of z in the region of interest to a threshold value (e.g., 0.003 in. (0.0762 mm)) and identify that surface point as the point of interest if its z value is equal to or above the threshold indicating that the surface point is far enough from the reference surface to assume that the user is trying to identify a deepest point or a highest point. If the z value of the point of interest is below the threshold indicating that the surface point is not far enough from the reference surface to assume that the user is trying to identify a deepest point or a highest point, it is not a valid highest or lowest point and the fourth cursor 234, 534 is not automatically placed at that location (FIGS. 5, 8).

In one embodiment, if the video inspection device 100 (e.g., the CPU 150) determines that the point of interest is a highest point (i.e., the surface point with the largest absolute value for z has a transformed actual z value that is positive), the video inspection device 100 (e.g., the CPU 150) can perform a check on that surface point to make sure it is a valid highest point with respect to the reference surface 250, 550. For example, if the video inspection device 100 (e.g., the CPU 150) determines that the highest point is on a surface that is substantially perpendicular (e.g., more than a 60 degree angle between the two surfaces) to the reference surface 250, 550, this would indicate that the highest point is on a vertical face (e.g., the side of a wall or on a turbine blade) and is not a valid highest point and the fourth cursor 234, 534 is not automatically placed at that location (FIGS. 5, 8).

In another embodiment, if the video inspection device 100 (e.g., the CPU 150) determines that the point of interest is a lowest or deepest point (i.e., the surface point with the largest absolute value for z has a transformed actual z value that is negative), the video inspection device 100 (e.g., the CPU 150) can perform a check on that surface point to make sure it is a valid lowest or deepest point with respect to the reference surface 250, 550. For example, if the video inspection device 100 (e.g., the CPU 150) determines that the lowest or deepest point is on a surface that is sloping downward relative to the reference surface 250, 550, the video inspection device 100 (e.g., the CPU 150) can, using a slope following algorithm, follow the slope downward from that surface point to the deepest point that was not a surface point whose normal line projection to the reference surface 250, 550 fell within the polygon formed by the three measurement points 221, 222, 223, 521, 522, 523 (FIGS. 5, 8).

Figure 11:
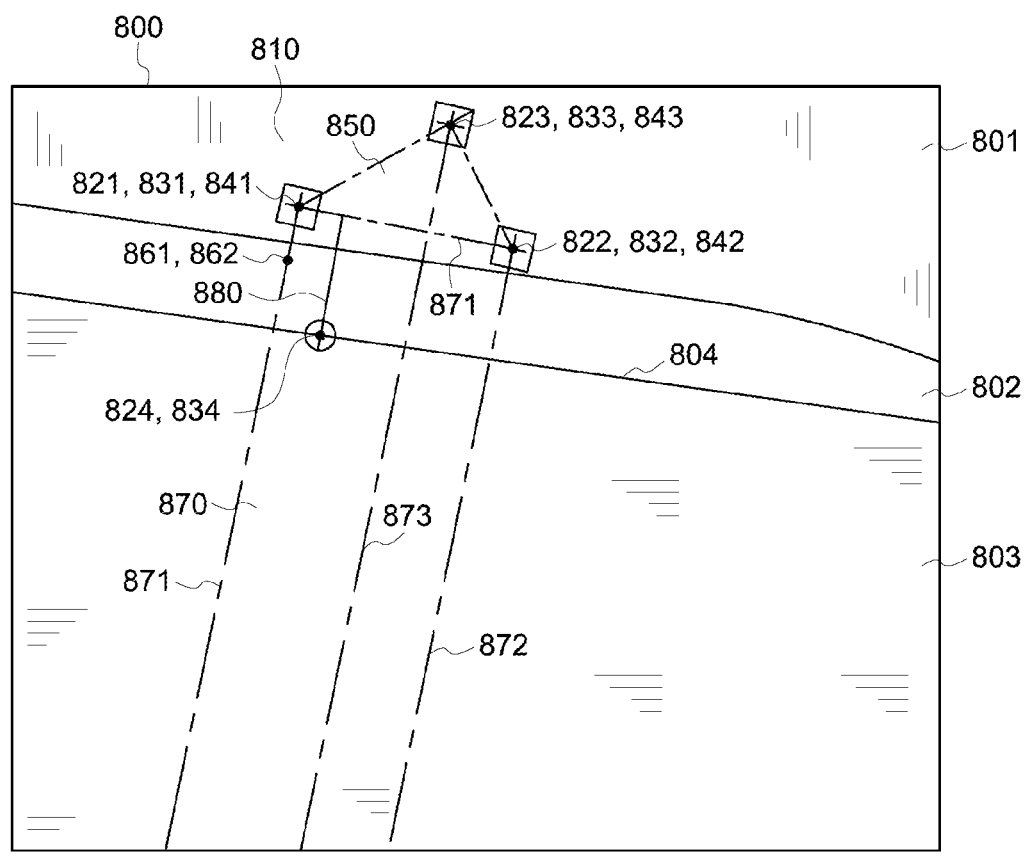
FIG. 11 is an exemplary image obtained by the video inspection device of a turbine engine blade and shroud in an exemplary embodiment.

In addition to using depth measurements for determining the deepest (or lowest) or highest points on the surface of a viewed objections, depth measurements can also be used to determine the clearance between the two surfaces. For example, FIG. 11 is another image 800 obtained by the video inspection device 100 of a turbine engine blade 803 (first surface) and the inner surface 810 of the turbine engine shroud 801 (second surface). As shown in FIG. 11, the operator can use the video inspection device 100 to obtain the image 800 and display it on a video monitor (e.g., an integral display 170 or external monitor 172). In one embodiment, the image 800 can be displayed in a measurement mode of the video inspection device.

The CPU 150 of the video inspection device 100 can then determine the three-dimensional coordinates in a first coordinate system of a plurality of surface points on the surface of the turbine engine blade 803 and the inner surface 810 of the turbine engine shroud 801, wherein the edge 804 of the turbine engine blade 803 and the inner surface 810 of the turbine engine shroud 801 have a gap 802 between them and are not parallel to each other. In one embodiment, the video inspection device can generate three-dimensional data from the image 800 in order to determine the three-dimensional coordinates. As discussed above, several different existing techniques can be used to provide the three-dimensional coordinates of the points on the image 800 (e.g., stereo, scanning systems, structured light methods such as phase shifting, phase shift moiré, laser dot projection, etc.).

As shown in FIG. 11, an operator can use the joystick 180 (or other pointing device (e.g., mouse, touch screen)) of the video inspection device 100 (FIG. 1) to select a plurality of reference surface points 821, 822, 823 on the inner surface 810 of the turbine engine shroud 801 to conduct a particular type of measurement. In one embodiment and as shown in FIG. 11, a total of three reference surface points 821, 822, 823 are selected on the inner surface 810 of the turbine engine shroud 801 to conduct a depth measurement of the clearance between the edge 804 of the turbine engine blade 803 and the turbine engine shroud 801. In one embodiment, the plurality of reference surface points 821, 822, 823 on the inner surface 810 of the turbine engine shroud 801 can be selected by placing reference surface cursors 831, 832, 833 (or other pointing devices) on pixels 841, 842, 843 of the image 800 corresponding to the plurality of reference surface points 821, 822, 823 on the inner surface 810. In the exemplary depth measurement, the video inspection device 100 can determine the three-dimensional coordinates in the first coordinate system of each of the plurality of reference surface points 821, 822, 823.

As shown in FIG. 11, the CPU 150 of the video inspection device 100 can determine a reference surface 850. In the exemplary depth measurement shown in FIG. 11, the three-dimensional coordinates of three or more surface points proximate one or more of the three reference surface points 821, 822, 823 can be used to determine a reference surface 850 (e.g., a plane). As discussed above, in one embodiment, the video inspection device 100 can perform a curve fitting of the three-dimensional coordinates in the first coordinate system of the three reference surface points 821, 822, 823 to determine an equation for the reference surface 850 (e.g., for a plane) as described in equation (1) above. In one embodiment, the video inspection device 100 (e.g., the CPU 150) can perform a curve fitting of the three-dimensional coordinates of the surface points associated with the pixels in the vicinity of reference surface cursors 831, 832, 833 to determine an equation for the reference surface 1020 (e.g., for a plane) as described in equation (1) above. In another embodiment, the curve fitting may use only the three-dimensional coordinates of the surface points associated with the pixels in the vicinity of only one of the reference surface cursors 831, 832, 833 for the reference surface 850.

As shown in FIG. 11, in order to determine the region of interest 870 to conduct a depth measurement of the clearance between the edge 804 of the turbine engine blade 803 and the turbine engine shroud 801, the CPU 150 of the video inspection device 100 computes the three-dimensional coordinates of an offset reference point 861 that is offset from the reference surface 850 in a positive direction toward the turbine engine blade 803 and is on a line that is normal to the reference surface 850 and passes through the first reference surface point 821 and cursor 831. In one embodiment, a coordinate transformation can be performed such that the transformed z value for all points on the reference surface 850 is z=0. The offset reference point 861 can then be located some nominal distance (e.g., 1.0 mm) in the z direction from the three-dimensional coordinates of the first reference surface point 821. The CPU 150 of the video inspection device 100 then determines the two-dimensional pixel 862 corresponding to the offset reference point 861 and determines a two-dimensional boundary line direction from the first reference surface cursor 831 to the two-dimensional pixel 862 of the offset reference point 861. The CPU 150 of the video inspection device 100 then determines three two-dimensional parallel region of interest boundary lines 871, 872, 873 that are in the boundary line direction and each pass through one of the three reference surface cursors 831, 832, 833 and go the edge of the image 800. The region of interest 870 is the region in the image 800 bounded by the two outermost region of interest boundary lines 871, 872 and in the positive direction of the line 874 between the first and second reference surface cursors 831, 832 through which the region of interest boundary lines 871, 872 pass.

In one embodiment, the video inspection device 100 (e.g., the CPU 150) can analyze the two-dimensional and/or three-dimensional data (e.g., three dimensional coordinates) of the surface points within the region of interest 870 to determine what particular depth measurement application (e.g., tip clearance measurement) the user is performing prior to automatically identifying the point of interest 824 (e.g., the edge point 824 on the edge 804 of the turbine engine blade 803) and placing the fourth cursor 834 at that location. For example, the video inspection device 100 (e.g., the CPU 150) can determine the distance from each of the surface points on the turbine engine blade 803 to the reference surface 850 on the inner surface 810 of the turbine engine shroud 801. In one embodiment, a histogram can be created of the number of surface points on the turbine engine blade 803 in the region of interest 870 having distances from the reference surface 870 in certain distance ranges (e.g., bins every 0.1 mm). The video inspection device 100 (e.g., the CPU 150) can also perform edge detection to identify the edge 804 of the turbine engine blade 803 that is perpendicular to the region of interest boundary lines 871, 872. When the image 800 is of the edge 804 of the turbine engine blade 803 and the inner surface 810 of the turbine engine shroud 801 having a gap 802 between them, the histogram shows that there are no surface points or data in the bins or distance ranges close to the reference surface 850 and then significant surface points and data beginning proximate to the edge 804 of the turbine engine blade 803, which results in the video inspection device 100 (e.g., the CPU 150) determining that the user is conducting a depth measurement for tip clearance. Once this is determined, the video inspection device 100 (e.g., the CPU 150) identifies as the point of interest a surface point on the edge 804 of the turbine engine blade 803 (i.e., edge point 824) and automatically places the edge point cursor 834 at that surface point. The tip clearance 880 is then determined as the distance between the point of interest/edge point 824 and the reference surface 850 on the inner surface 810 of the turbine engine shroud 801.

In view of the foregoing, embodiments of the invention automatically identify a point of interest in a depth measurement on a viewed object using a video inspection device. A technical effect is that the time to perform the depth measurement is reduced and the accuracy of the measurement is improved since the user does not need to manually identify the point of interest for a particular measurement application.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

To the extent that the claims recite the phrase "at least one of" in reference to a plurality of elements, this is intended to mean at least one or more of the listed elements, and is not limited to at least one of each element. For example, "at least one of an element A, element B, and element C," is intended to indicate element A alone, or element B alone, or element C alone, or any combination thereof. "At least one of element A, element B, and element C" is not intended to be limited to at least one of an element A, at least one of an element B, and at least one of an element C.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for automatically identifying a point of interest in a depth measurement of a viewed object, the method comprising the steps of:
    displaying on a monitor an image of the viewed object;
    determining the three-dimensional coordinates of a plurality of points on a surface of the viewed object using a central processor unit;
    determining a reference surface using the central processor unit;
    determining at least one region of interest that includes a plurality of points on the surface of the viewed object using the central processor unit;
    determining a distance between each of the plurality of points on the surface of the viewed object in the at least one region of interest and the reference surface using the central processor unit;
    determining the point of interest as the point on the surface of the viewed object in the at least one region of interest having the greatest distance from the reference surface using the central processor unit; and
    determining if the point of interest is on a surface that is substantially perpendicular to the reference surface.

2. The method of claim 1, further comprising the step of displaying on the monitor a graphical indicator at the location of the point of interest on the surface of the viewed object.

3. The method of claim 1, further comprising the step of comparing the distance of the point of interest from the reference surface to a threshold.

4. The method of claim 1, wherein the point of interest on the surface of the viewed object in the at least one region of interest is protruding relative to the reference surface.

5. A method for automatically identifying a point of interest in a depth measurement of a viewed object, the method comprising the steps of:
    displaying on a monitor an image of the viewed object;
    determining the three-dimensional coordinates of a plurality of points on a surface of the viewed object using a central processor unit;
    determining a reference surface using the central processor unit;
    determining at least one region of interest that includes a plurality of points on the surface of the viewed object using the central processor unit;
    determining a distance between each of the plurality of points on the surface of the viewed object in the at least one region of interest and the reference surface using the central processor unit;
    determining the point of interest as the point on the surface of the viewed object in the at least one region of interest having the greatest distance from the reference surface using the central processor unit; and
    determining if the point of interest is on a surface that is sloping downward relative to the reference surface.

6. The method of claim 5, further comprising the step of displaying on the monitor a graphical indicator at the location of the point of interest on the surface of the viewed object.

7. The method of claim 6, wherein the graphical indicator is a cursor.

8. The method of claim 5, further comprising the step of comparing the distance of the point of interest from the reference surface to a threshold.

9. The method of claim 5, wherein the step of determining a reference surface comprises:
    selecting a plurality of reference surface points on the surface of the viewed object using a pointing device; and
    performing a curve fitting of the three-dimensional coordinates of the plurality of reference surface points.

10. The method of claim 5, wherein the reference surface is one of a plane, a cylinder, and a sphere.

11. The method of claim 5, wherein the step of determining a distance between each of the plurality of points on the surface of the viewed object in the at least one region of interest and the reference surface comprises determining the distance of a line extending between the reference surface and each of the plurality of points, wherein the line perpendicularly intersects the reference surface.

12. The method of claim 5, wherein the point of interest on the surface of the viewed object in the at least one region of interest is recessed relative to the reference surface.

13. A method for automatically identifying a point of interest in a depth measurement of a viewed object having a first surface and a second surface that have a gap between them and are not parallel to each other, the method comprising the steps of:
    displaying on a monitor an image of the viewed object;
    determining the three-dimensional coordinates of a plurality of points on the first surface and the second surface of the viewed object using a central processor unit;
    determining a reference surface on the first surface of the viewed object using the central processor unit;
    determining at least one region of interest that includes a plurality of points on the second surface of the viewed object using the central processor unit;
    determining a distance between each of the plurality of points on the second surface of the viewed object in the at least one region of interest and the reference surface using the central processor unit; and
    determining the point of interest as a point on an edge of the second surface of the viewed object using the central processor unit.

14. The method of claim 13, further comprising the step of displaying on the monitor a graphical indicator at the location of the point of interest on the second surface of the viewed object.

15. The method of claim 14, wherein the graphical indicator is a cursor.

16. The method of claim 13, wherein the viewed object is a turbine engine, the first surface of the viewed object is an inner surface of a shroud of the turbine engine, and the second surface of the viewed object is a turbine engine blade.

17. The method of claim 13, wherein the step of determining a reference surface comprises:
  selecting a plurality of reference surface points on the first surface of the viewed object using a pointing device; and
  performing a curve fitting of the three-dimensional coordinates of the plurality of reference surface points.

18. The method of claim 13, wherein the reference surface is one of a plane, a cylinder, and a sphere.

19. The method of claim 13, wherein the step of determining a distance between each of the plurality of points on the second surface of the viewed object in the at least one region of interest and the reference surface comprises determining the distance of a line extending between the reference surface and each point, wherein the line perpendicularly intersects the reference surface.

* * * * *